(12) United States Patent
Chan et al.

(10) Patent No.: US 11,938,417 B2
(45) Date of Patent: Mar. 26, 2024

(54) METHODS AND SYSTEMS FOR REMOVING PRESSURE AND AIR FROM CHROMATOGRAPHY COLUMNS

(71) Applicant: Repligen Corporation, Waltham, MA (US)

(72) Inventors: Alan Kit Ho Chan, Quincy, MA (US); James Ronald Peyser, North Billerica, MA (US)

(73) Assignee: REPLIGEN CORPORATION, Waltham, MA (US)

( * ) Notice: Subject to any disclaimer, the term of this patent is extended or adjusted under 35 U.S.C. 154(b) by 85 days.

(21) Appl. No.: 17/836,412

(22) Filed: Jun. 9, 2022

(65) Prior Publication Data
US 2022/0297029 A1 Sep. 22, 2022

Related U.S. Application Data

(62) Division of application No. 16/137,376, filed on Sep. 20, 2018, now Pat. No. 11,389,748.

(Continued)

(51) Int. Cl.
*B01D 15/10* (2006.01)
*A61L 2/08* (2006.01)
(Continued)

(52) U.S. Cl.
CPC ............. *B01D 15/10* (2013.01); *B01D 15/20* (2013.01); *B01D 15/362* (2013.01); *B01J 39/04* (2013.01);
(Continued)

(58) Field of Classification Search
CPC ........ B01D 15/14; B01D 15/10; B01D 15/18; G01N 30/38; G01N 2030/382; G01N 2030/385; B67D 1/12; B67D 1/1277
See application file for complete search history.

(56) References Cited

U.S. PATENT DOCUMENTS

| 6,123,849 A | 9/2000 | Purdom |
| 7,052,603 B2 | 5/2006 | Schick |

(Continued)

FOREIGN PATENT DOCUMENTS

| WO | 2007067882 A2 | 6/2007 |
| WO | 2008110291 A1 | 9/2008 |

(Continued)

*Primary Examiner* — Ryan B Huang
(74) *Attorney, Agent, or Firm* — KDW Firm PLLC

(57) ABSTRACT

Methods and systems for removing gases and/or pressure formed during the sterilization, e.g., the gamma irradiation, of prepacked chromatography systems (column plus attached tube and valve set) are described. The methods include purging the gas and/or pressure through specially designed tube and valve sets without breaching the sterility of the prepacked sterile chromatography system. The systems include a sterile or aseptic pre-packed chromatography column including a column having an inlet and an outlet, a tubing and valve set attached to the inlet and the outlet, and a pump configured to pump sterile or aseptic liquid from the fluid source along the tubing and valve set, into the column tube inlet and out of the column tube outlet along a first flow path, thereby removing any entrapped gas and/or pressure from the chamber.

19 Claims, 29 Drawing Sheets

Related U.S. Application Data

(60) Provisional application No. 62/561,575, filed on Sep. 21, 2017.

(51) Int. Cl.
  *B01D 15/20*  (2006.01)
  *B01D 15/36*  (2006.01)
  *B01J 39/04*  (2017.01)
  *B01J 39/19*  (2017.01)
  *B01J 39/26*  (2006.01)
  *G01N 30/50*  (2006.01)
  *G01N 30/60*  (2006.01)

(52) U.S. Cl.
  CPC ............... *B01J 39/19* (2017.01); *B01J 39/26* (2013.01); *G01N 30/50* (2013.01); *G01N 30/6034* (2013.01); *A61L 2/081* (2013.01)

(56) References Cited

U.S. PATENT DOCUMENTS

| | | | |
|---|---|---|---|
| 10,119,970 B2 * | 11/2018 | Miltenyi | ............ B01D 15/3809 |
| 2003/0098280 A1 | 5/2003 | Davis | |
| 2003/0230521 A1 | 12/2003 | Schick | |
| 2008/0017580 A1 * | 1/2008 | Gebauer | ................ G01N 30/56 |
| | | | 210/656 |
| 2008/0142439 A1 | 6/2008 | Berglof | |
| 2009/0184052 A1 | 7/2009 | Agren | |
| 2010/0193441 A1 | 8/2010 | Agee | |
| 2013/0193052 A1 | 8/2013 | Witt | |
| 2016/0325204 A1 | 11/2016 | Peyser | |

FOREIGN PATENT DOCUMENTS

| | | | |
|---|---|---|---|
| WO | 2009157852 A1 | 12/2009 | |
| WO | 2015109246 A1 | 7/2015 | |

* cited by examiner

METHODS AND SYSTEMS FOR REMOVING PRESSURE AND AIR FROM CHROMATOGRAPHY COLUMNS

CLAIM OF PRIORITY

This application is a divisional of U.S. nonprovisional patent application Ser. No. 16/137,376 filed Sep. 20, 2018, which claims the benefit of and priority under 35 U.S.C. § 119 to U.S. provisional patent application Ser. No. 62/561,575, filed Sep. 21, 2017, the entirety of which applications are incorporated by reference herein for all purposes.

TECHNICAL FIELD

This invention relates to methods and system for making aseptic connections for chromatograph columns while providing the ability to remove any pressure and air trapped within the columns.

BACKGROUND

Column chromatography is a separation and/or purification technique in which a stationary "bed" of a packing medium is contained within a rigid tube. The packing medium can be in the form of particles of a solid ("stationary phase") or a solid support material coated with a liquid stationary phase. Either way, the packing medium typically fills the inside volume of the column tube.

In separation chromatography, as a liquid sample ("mobile phase") passes through the column, different compounds in the sample can associate differentially with the stationary phase (e.g., packing medium) such that they are slowed relative to the mobile phase and move through the column at different speeds. Thus, those compounds that associate more with the stationary phase move more slowly through the column than those that associate less, and this speed differential results in the compounds being separated from one another as they pass through the column. Features of the stationary phase that promote differential association can be, e.g., ionic charge (ion exchange chromatography), hydrophobicity (hydrophobic interaction chromatography), and porosity (size exclusion chromatography).

In another type of column chromatography, affinity chromatography, the packing medium includes binding agents, such as antigens, antibodies, or ligands, that specifically bind to one or more desired compounds or molecules in the liquid sample. Thus, as the liquid sample flows through the packing medium, only the desired compounds or molecules remain in the column. A subsequent flow through the packing medium of an eluting liquid separates the desired compounds or molecules from the binding agents attached to the packing medium, or separates the binding agents from the packing medium. Either way, the desired compounds or molecules are rinsed out of the column and collected in the eluting fluid. Affinity chromatography can be used in a number of applications, including nucleic acid purification, protein purification from cell free extracts, and purification from blood.

The main components of a chromatography column are the tube, which is often made of a metal, glass, or highly rigid plastic material, and a pair of flow distributors, which are typically inserted into the two ends of the tube to form a space or chamber in the tube between the flow distributors into which the packing medium is loaded. The flow distributors are designed with integrated porous surfaces such as screens, mesh, or frits that retain the chromatography media.

Chromatography columns can be pre-packed and used upon demand for development and commercial bioprocess manufacturing. These columns are produced and fixed in bed height such that flow distributors are irreversibly aligned within the chromatography tube. New developments in bioprocessing, such as continuous processing, or multi-product facilities, require increased stringency in microbial control. Aseptic connection strategies and flow paths from cell culture into downstream purification are essential to reduced risk of contamination. Sterilization by steam and radiation has been applied to disposable bioreactors, flow paths, and recently chromatography columns for biologics purification. However, in some instances off-gassing of the packing medium solution can occur during the gamma irradiation process, creating gas pockets and pressurization within the column's packed bed. In this case, the packed bed can negatively affect the fluid flow dynamics. Thus, there is a need to design a pre-packed chromatography column that is aseptic or sterile and free of gasses and that does not impair the separation performance of the column or increase the risk of increasing unwanted bioburden during normal use of the column.

SUMMARY

The invention is based, at least in part, on the discovery that if you connect a tubing and valve system as specified herein to a pre-packed chromatography column to create a closed system, you can then sterilize the closed system, e.g., with gamma irradiation, and thereafter use the tubing and valve system to simply and easily purge any gas bubbles and/or pressure that may have formed inside the closed system during sterilization and yet maintain sterility of the closed system. As a result, the new systems and methods can maintain the performance of the packed column and avoid disruption of the chromatography flow path during use due to bubbles and/or pressure formed from off-gassing within the column during irradiation and prior to use.

The columns can be packed with chromatography media of various types and can be used to manufacture biologics. Pre-packed columns prepared according to this invention can be sterilized by a gamma radiation dose greater than or equal to 8 kGy. Functional fluid distribution (e.g., measured by Height Equivalent to the Theoretical Plate (HETP) or HETP and asymmetry testing) following gamma irradiation is similar to original values following gas removal.

The present disclosure describes the functionality of efficient priming of the connected lines and then providing backflow, also known as upflow (e.g., flow in reverse to the typical direction of forward flow during column use without having to have a chromatography system capable of reverse flow) to the column to remove entrapped air and restore the packed bed. The effluent flow can exit via an outlet, it can exit via a fluid path connected to a sterile or aseptic filter, or it can be collected in an expansion bag attached for that purpose. A sterilizing grade hydrophobic vent filter could also be incorporated to relive pressure build up or to evacuate trapped gasses. This vent filter in combination with a check valve would ensure venting in one direction without backflow into the system.

In one aspect, the present disclosure provides methods of removing entrapped gas, pressure, or both gas and pressure from a pre-packed chromatography column that comprises a column tube having a column tube inlet and a column tube outlet and first and second flow distributors arranged within the column tube to form a chamber filled with a packing medium. The methods include (a) obtaining a tubing and valve set comprising tubing and at least one valve configured to define at least two different fluid paths through the tubing; (b) either: (i) attaching tubing of the tubing and valve set to the column tube inlet and the column tube outlet and then sterilizing the connected pre-packed chromatography column and the tubing and valve set, or (ii) sterilizing the pre-packed chromatography column and the tubing and valve set individually and then attaching the sterile tubing of the tubing and valve set to the sterile column tube inlet and the sterile column tube outlet in a manner that maintains sterility of both the column and the tubing and valve set; (c) attaching the sterile tubing and valve set to a sterile or aseptic fluid source and to a fluid outlet; and (d) pumping sterile or aseptic liquid from the sterile or aseptic fluid source along the tubing and valve set, wherein the at least one valve is in a first position, into the column tube inlet and out from the column tube outlet along a first flow path, thereby removing any entrapped gas, pressure, or both gas and pressure from the chamber, the tubing, and the at least one valve along the first flow path without breaching the sterility of the pre-packed chromatography column and the tubing and valve set.

In these methods, attaching the sterile tubing of the tubing and valve set to the sterile column tube inlet and the sterile column tube outlet in a sterile manner can include using aseptic or sterile connectors or weldable tubing. In these methods, the sterilizing can be achieved with irradiation, e.g., with gamma radiation. For example, by applying a gamma radiation dose of at least 8 kGy.

In some embodiments, attaching tubing to the column tube inlet and the column tube outlet includes connecting ends of the tubing to a connector fixed to the column tube inlet and to a connector fixed to the column tube outlet. For example, the connectors can be screwed into, clamped onto, or welded to the column tube inlet and to the column tube outlet.

In certain implementations, the methods can further include moving the at least one valve from the first position to a second position to direct the sterile or aseptic liquid along a second flow path. In other implementations, the methods further include moving the at least one valve from the first position to a second position and pumping sterile or aseptic liquid from the sterile or aseptic liquid source into the column tube outlet, through the pre-packed column tube, and out of the column inlet. For example, these methods can include pumping a volume of sterile or aseptic liquid equivalent to 0.1, 0.2, 0.3, 0.4, 0.5, or more volumes of the chamber.

In some embodiments, the methods further include attaching the tubing to a sterile or aseptic filter and pumping sterile or aseptic liquid through the sterile or aseptic filter. In some implementations, the methods can further include collecting the sterile or aseptic liquid pumped through the sterile or aseptic filter and testing one or more properties of the sterile or aseptic liquid.

In some implementations, the methods can include venting pressure from the tubing and valve set with a vent filter. In some implementation, the methods further include attaching tubing from the tubing and valve set to an expansion bag.

In some embodiment, the methods are used with column tubes that are pre-packed for a single use and that are disposable. In general, the methods can be used when the pre-packed chromatography column and tubing and valve set are connected to a chromatography system.

In another aspect, the disclosure features systems for aseptic purification of biomolecules. The systems include a sterile pre-packed chromatography column comprising a column tube having a column tube inlet and a column tube outlet and first and second flow distributors arranged within the column tube to form a chamber filled with a packing medium; a sterile tubing and valve set attached to the column tube inlet and the column tube outlet, wherein the tubing and valve set comprises tubing and at least one valve configured to define at least two different fluid paths fluidly connected to the column tube inlet and the column tube outlet; and a pump configured to pump sterile or aseptic liquid from a sterile or aseptic fluid source along the sterile tubing and valve set, wherein the at least one valve comprises a first position that enables the sterile or aseptic liquid to flow into the column tube inlet and out of the column tube outlet along a first flow path to remove any entrapped gas, pressure, or both gas and pressure from the chamber, the tubing, and the at least one valve along the first flow path.

In these systems, the sterile column can be pre-packed with resin and the column, resin, and tubing have a sterility assurance level (SAL) of $10^{-3}$ or better. In some implementations, the systems further include a controller configured and arranged to control the pump and the position of the at least one valve. For example, in some embodiments, the controller includes a processor and a memory storing instructions for execution by the processor for opening and closing the at least one valve.

In some embodiments, the systems further include connectors at the column inlet and outlet configured to form sterile or aseptic connections and to permit fluid to flow through the chamber formed between the first and second flow distributors. For example, in some embodiments the connectors are pre-installed to form sterile or aseptic connections with the tubing and valve set.

In certain implementations, the systems further include a second pump fluidly attached to the tubing and valve set. In some implementations, the systems further include a vent filter arranged in the tubing and valve set to enable venting gas, pressure, or gas and pressure from the pre-packed chromatography column and the tubing and valve set. For example, such vent filters can be or include a hydrophobic vent filter and a check valve.

In certain embodiments or these systems, the chromatography column tube is formed of one or more of stainless steel, glass, polypropylene (PP), polyethylene (PE), polyamides, acetals, or glass-filled or carbon-filled plastics or elastomeric components. In different embodiments, the chromatography packing medium is one of glass, plastic, cellulose, agarose, ceramic, or polymer, in the form of rough particles, fibers, membranes, or beads. In certain implementations, the chromatography column tubes are pre-packed for a single use and are disposable.

In some instances, the chromatography column with attached tubing and valve set as described herein can be attached to a chromatography system (e.g., AKTA™ Ready, GE Healthcare) through an aseptic or sterile connection or by welding. Any over-pressure and/or gasses or bubbles in the chromatography column and tubing and valve set cause by the sterilization process, e.g., by gamma irradiation, can be vented through the chromatography system by opening the valve set or using a priming sequence described herein.

In some instances, the tubing is weldable to form closed process flow paths. The tubing and valve set can form an aseptic or sterile connection pre- or post-gamma irradiation.

As used herein, the terms "resin," "separation media," "chromatography media," and "medium" all refer to particles suspended in a liquid that are used to fill chromatography columns. Examples of these resins include materials made of glass, plastics, polymers, cellulose, agarose, and other substances. The resins may be rough particles or beads. The beads may be monodispersed or have a population of sizes and may vary, for example, from 15 µm to 200 µm in size. The resin may be modified to contain various substituents that affect binding to the particles to achieve separation of proteins and other substances in a feed stream. The substituents may be positively or negatively charged, or hydrophobic, or a specific affinity moiety (such as protein A) or a combination of these properties. In some instances, the chromatography columns are filled with fibers, membranes, or monoliths that are retained with a fluid distribution system.

As used herein, the term "connector" refers to a joining device that enables an aseptic or sterile connection, for example, either a mechanical mating or one or more locations suitable for joining with a sterile or aseptic tubing weld.

As used herein, the term "aseptic" refers to a condition or process designed to reduce the likelihood of contamination from pathogens (e.g., pathogenic bacteria, viruses, fungi, and/or parasites or harmful spores).

The term "sterile" generally refers to a condition or process designed to achieve an environment that is free or essentially free from all living microorganisms (harmful or otherwise) and their spores. As used herein, "sterile" means a sterility assurance level (SAL) of $10^{-3}$ or better.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control.

In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

Figure 1A:
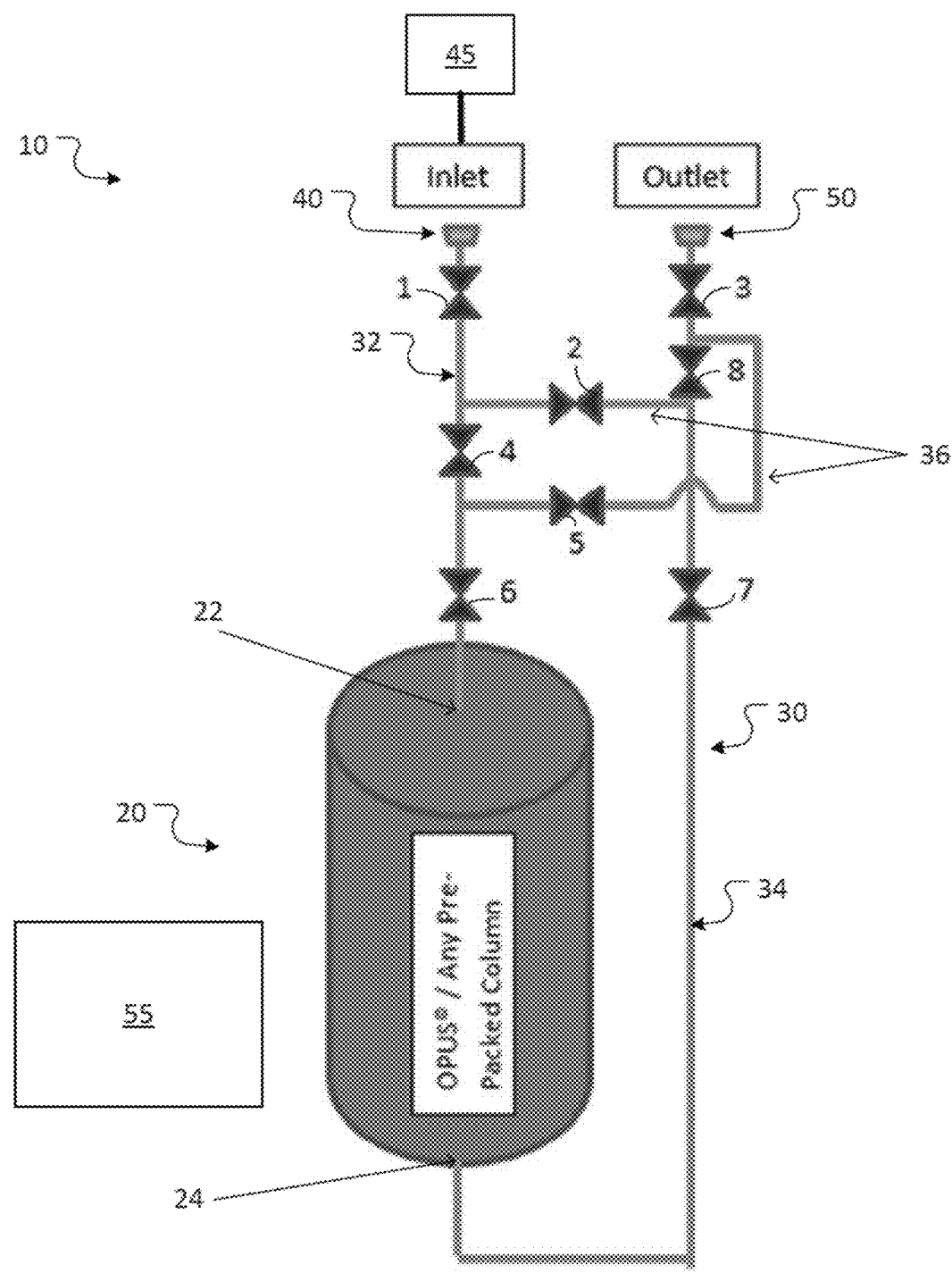
FIGS. 1A-E are schematic diagrams of an embodiment of a sterile or aseptic chromatography column and associated system of valves and tubing forming fluid flow paths of a closed system connected to the column, as described herein.

The present disclosure describes new methods and systems for gamma irradiation of pre-packed chromatography columns arranged in closed systems including a series of valves and tubing, where the performance through the packed column bed remains suitable for its intended use and wherein the system of valves and tubing can be used to purge gas from the closed systems that may arise during sterilization, e.g., by gamma irradiation.

Pre-packed or disposable chromatography columns can be sterilized by gamma radiation and are shown to maintain packed bed integrity, e.g., as measured by pulse injection of a non-interacting small molecule. However, in some instances off-gassing of the packing medium solution can occur during the gamma irradiation process, creating undesirable gas of air pockets or bubbles and/or pressure within the column's packed bed and connected sterile or aseptic tubing that can negatively affect the fluid flow dynamics. In some instances, pressurization of the columns occurs. The current disclosure solves the problem of the trapped pressure, gas, or air by the use of tubing and valve systems and vent filters installed to the inlet and outlet of the pre-packed column. These tubing, valve systems, and vents permit a closed aseptic connection to the chromatography system, allowing for the removal of entrapped gas from the column while maintaining a closed system and sterility. These tubing valve systems and venting methods result in pre-packed columns that have packed bed performance comparable to original pre-irradiation values. The tubing can be any type of tubing, such as silicone, braided/silicone, C-FLEX®, etc.

Disruption of the chromatography flow path due to bubbles and/or pressure from off-gassing within the column can thus be avoided. The columns can be packed, for example, with chromatography media with a silica, agarose, ceramic, or polymeric backbone, which can be functionalized with an affinity ligand (e.g., protein A—recombinant native structure, or engineered functional domains), ionic interaction ligands, mixed mode ligands, or hydrophobic ligands. Columns are packed and stored in aqueous buffers that may contain organic components (e.g., 2% benzyl alcohol, 20% ethanol). These columns can be used to manufacture biologics such as proteins, viruses, virus-like particles, exosomes, and others. Pre-packed columns prepared as described herein are sterilized by a gamma radiation dose typically greater than or equal to 8 kGy. Functional fluid distribution measured by Height Equivalent to the Theoretical Plate (HETP) and asymmetry tests following gamma irradiation show values similar to original values following gas removal.

Chromatography Columns

The column tubes are hollow, cylindrical members, and are typically round cylinders that permit a fluid (e.g., a liquid) to flow from a first end (e.g., an upper end) to a second end (e.g., a lower end). The inner diameter of the tubes are sized and configured to receive flow distributors for delivering fluid to and removing fluid from the tube. Based on various chromatography column performance specifications, the tubes can be made in a variety of different sizes and configurations and include the OPUS® line of chromatography columns and other columns used in biopharmaceutical applications (Repligen Corp., Waltham, Mass.).

The chromatography components described herein can be made from any of various structurally and chemically suitable materials. For example, the components can be made from various plastics, such as thermoplastics (e.g., acrylonitrile butadiene styrene (ABS), acrylic (PMMA), polypropylene (PP), polyvinyl chloride (PVC), polytetrafluoroethylene (PTFE), other thermoplastics, or composites) and thermosetting plastics (e.g., epoxy resins, and fiber reinforced plastics. The columns can be also made entirely from metals, e.g., stainless steel, or from other glass or rigid plastics such as polyamides (such as various nylons), acetals, or glass-filled or carbon-filled plastics, e.g., glass-fiber and carbon-fiber plastics) or elastomeric components. Material selection considerations can include the specific mechanical properties of the materials and whether the materials will withstand the induced internal operating pressures of the system. The columns' design is such that they can be packed with various types of chromatography packing media, e.g., resins, other porous or non-porous materials to a "bed height" with infinite variability between 0 and 50 cm and longer. The internal diameter can be, for example, but not limited to, 5, 8, 10, 12.6, 15, 20, 25, 30, 40, 50, or 60 cm or larger, up to about 80, 90, or 100 cm, or larger.

The flow distributors used in these columns are in the form of a cylindrical disc with one or more inlet/outlet openings that enable liquids to flow into and through the disc. In addition, the flow distributors can include a bed support, screen, and/or filter that is attached to the packing medium side of the flow distributor disc. The column also may or may not incorporate O-rings between the flow distributors and the inner wall of the column tube. The flow path of the flow distributors can be designed according to standard practices and known designs, and the flow distributors themselves can be made, for example, of the same or a similar plastic material as the tubes, but can also be made of metal, ceramics, and other rigid materials that are inert to the liquids and reagents that are to be flowed through the columns.

The tubes of the chromatography columns described herein can be packed with any solid phase medium material that is used in column chromatography as specified by the end-user. This diversity of potential packing medium materials extends to both the composition of base particles as well as their functional chemistries (e.g., affinity, ion exchange, and hydrophobic interaction). Packing medium materials can include a slurry of stationary phase particles added to a mobile phase liquid or solvent. Stationary phase particles can include silica gel ($SiO_2$), ceramic, alumina ($Al_2O_3$), cellulose, agarose, polymeric and other suitable materials in various particle sizes. The mobile phase can include one or more of various solvents, such as deionized water, buffered salt solutions, ethanol, or other common solutions used for chromatographic separations.

Systems of Valves and Tubing for Removal of Gases

The tubing and valve sets described herein for removal of gases and priming of a chromatography column can be attached to an OPUS® column or any chromatography column in a pre-packed format that can be gamma irradiated for sterilization purposes. Generally, a radiation dose of 8 kGy or greater is effective. In some implementations, a dose range of 25-45 kGy can be used. As described above, the columns are constructed of materials that are able to withstand such irradiation. Additionally, the tubing and valve sets connected to the columns are also constructed of gamma-stable materials.

FIG. 1A shows a sterile or aseptic chromatography column system 10 that can be used for the sterile or aseptic purifying of biomolecules (e.g., proteins such as antibodies, viruses, virus-like particles, exosomes, etc.). A chromatography column 20, such as an OPUS® column, is attached to a tubing and valve system or set 30. An upstream tubing portion 32 of the tubing set 30 is attached to a fluid source or fluid inlet 40 at one end and to a column inlet 22 at another end. An additional part of the tubing set 30, the downstream tubing portion 34, is attached to a fluid sink or fluid outlet 50 at a first end and to a column outlet 24 at its second end. The tubing and valve set 30 includes additional tubing branches 36. These tubing branches 36 can connect the upstream tubing 32 to the downstream tubing 34 to create multiple flow paths for liquid flowing through the tubing and valve set 30.

The column inlet 22 and column outlet 24 are connectors that attach to the column 20 and to the tubing and valve system 30. In some instances, the connectors of column inlet 22 and column outlet 24 are integral with the column 20. In other instances, the connectors of column inlet 22 and column outlet 24 are integral with the tubing and valve system 30. The connectors of column inlet 22 and column outlet 24 can attach the tubing and valve set 30 to the column 20 in a sterile or aseptic manner. For example, the connectors of column inlet 22 and column outlet 24 can be welded to the column 20, and then can be gamma irradiated post-welding. Alternatively, the connectors of column inlet 22 and column outlet 24 can be welded to the tubing and valve set 30. In all instances, the tubing and valve set 30, the connectors of column inlet 22 and column outlet 24, and the column 20 can be gamma irradiated after they are attached to each other. In all instances, the tubing can be attached to the column before or after sterilization of the column. In some instances, the column 20 includes a weldable sterile or aseptic connection on inlet 22 and outlet 24, and the tubing and valve set 30 can include weldable tubing or a connector on the upstream tubing portion 32 and/or on the downstream tubing portion 34. In different scenarios, the weldable sterile or aseptic connectors are attached to column 20 and tubing set 30 before, during, or after the gamma irradiation process, and they enable an aseptic or sterile connection to be made and maintained.

The tubing and valve set 30 includes multiple valves, e.g., in FIG. 1A there are valves 1-8. The valves are positioned at various locations along the upstream 32 and downstream 34 portions of the tubing and valve set 30 as well as along the tubing branches 36. Opening and closing the valves 1-8 can permit or prevent fluid entering the tubing and valve set from the fluid inlet 40 from flowing along different portions of the tubing and valve set 30, e.g., opening and closing valves 1-8 directs fluid along different fluid paths that may include the upstream tubing and may or may not include the column 20, the downstream tubing 34 or one or more of the tubing branches 36. A controller 55 (shown schematically) can be connected to the valves 1-8 and pump 45 or (pumps) that propel the liquid through the tubing and valve set 30 from the fluid inlet 40. The controller 55 can synchronize the opening and closing of the valves 1-8 (or more valves, depending on the overall the system) and the speed of the pumps to perform the steps of priming and using the sterile or aseptic chromatography column system 10 as described below.

In some implementations, the new systems include valves, e.g., valves 1-8, with manual opening and closing abilities without a controller 55. In some implementations, the systems include a controller 55 that includes one or more processors and volatile or non-volatile memory containing software instructions for execution by the one or more processors that include software instructions for operating the valves and pumps. The software instructions are stored on any type of non-transitory computer-readable medium and are executable by the one or more processors to perform the instructions, including instructions to synchronize the opening and closing of the valves 1-8 (or more valves, depending on the overall the system) and the speed of the pumps to perform the steps of priming and using the sterile or aseptic chromatography column system 10 as described herein and as shown in the figures (e.g., FIGS. 1A to 1E, 2A to 2B, and 3A-3E), which show specific sequences of opening and closing difference valves according to different protocols for different sets of valves and different priming, upflow, and downflow sequences.

Figure 1B:
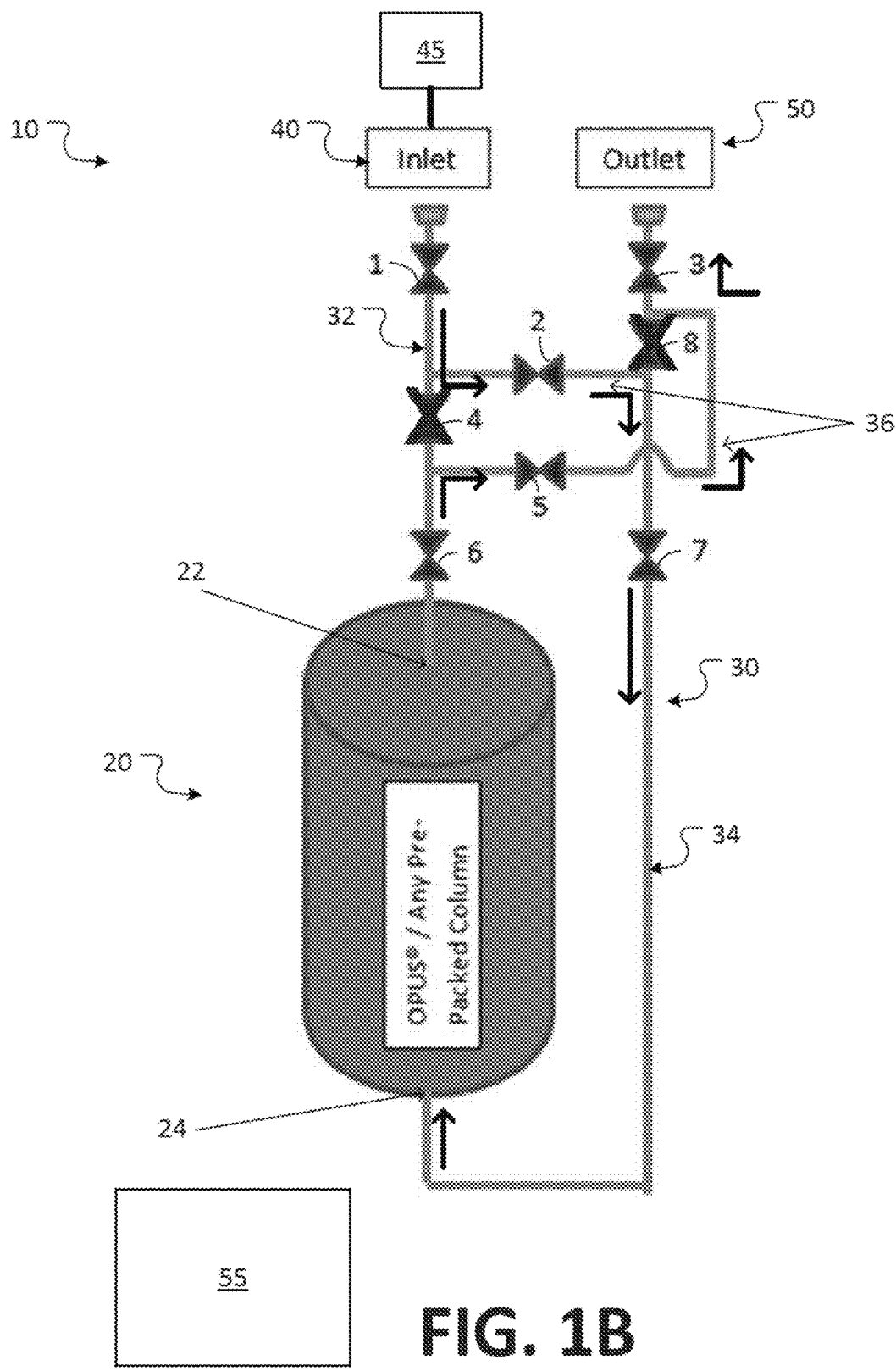

The sterile or aseptic chromatography column system 10 of FIGS. 1A to 1E can be used to prime the chromatography column 20 while removing any gas bubbles and/or pressure that might be present in the column 20, the tubing 30, and any connectors such as the column inlet 22 and column outlet 24. For example, a first priming sequence is shown in FIG. 1B. This first priming sequence provides priming initialization and upflow (e.g., backflow) conditioning of the column, as described below for forward flow pumps.

In FIG. 1B, valves 1, 2, 3, 5, 6, and 7 are open, while valves 4 and 8 are closed as indicated by the "X." This configuration permits flow through, e.g., down through, the upstream tubing 32, e.g., fluid flowing from the fluid inlet 40 downwards to prime upstream tubing 32. This configuration also permits upflow (e.g., backflow) conditioning of the column 20, e.g., flow from the column outlet 24 through the column 20, and out through inlet 22 and with the buffer or storage solution being used to prime the column 20 then exiting out of the fluid outlet 50. Typically, one or more column volumes (CVs) of fluid are pumped through the column (e.g., 1CV, 3 CVs, 5 CVs, or 10 CVs). Less than 1CV could also be effective. A column volume is defined as the volume of the chamber formed within the column tube between the first and second flow distributors and in this application is filled with a packing medium while the priming operation is taking place. As shown by the arrows in FIG. 1B, fluid proceeds from fluid inlet 40 along the upstream tubing 32 through the top tubing branch 36 to the downstream tubing 32, and then from column outlet 24 through the column 20, out from column inlet 22, along the bottom tubing branch 36 and exits the system at fluid outlet 50.

Figure 1C:
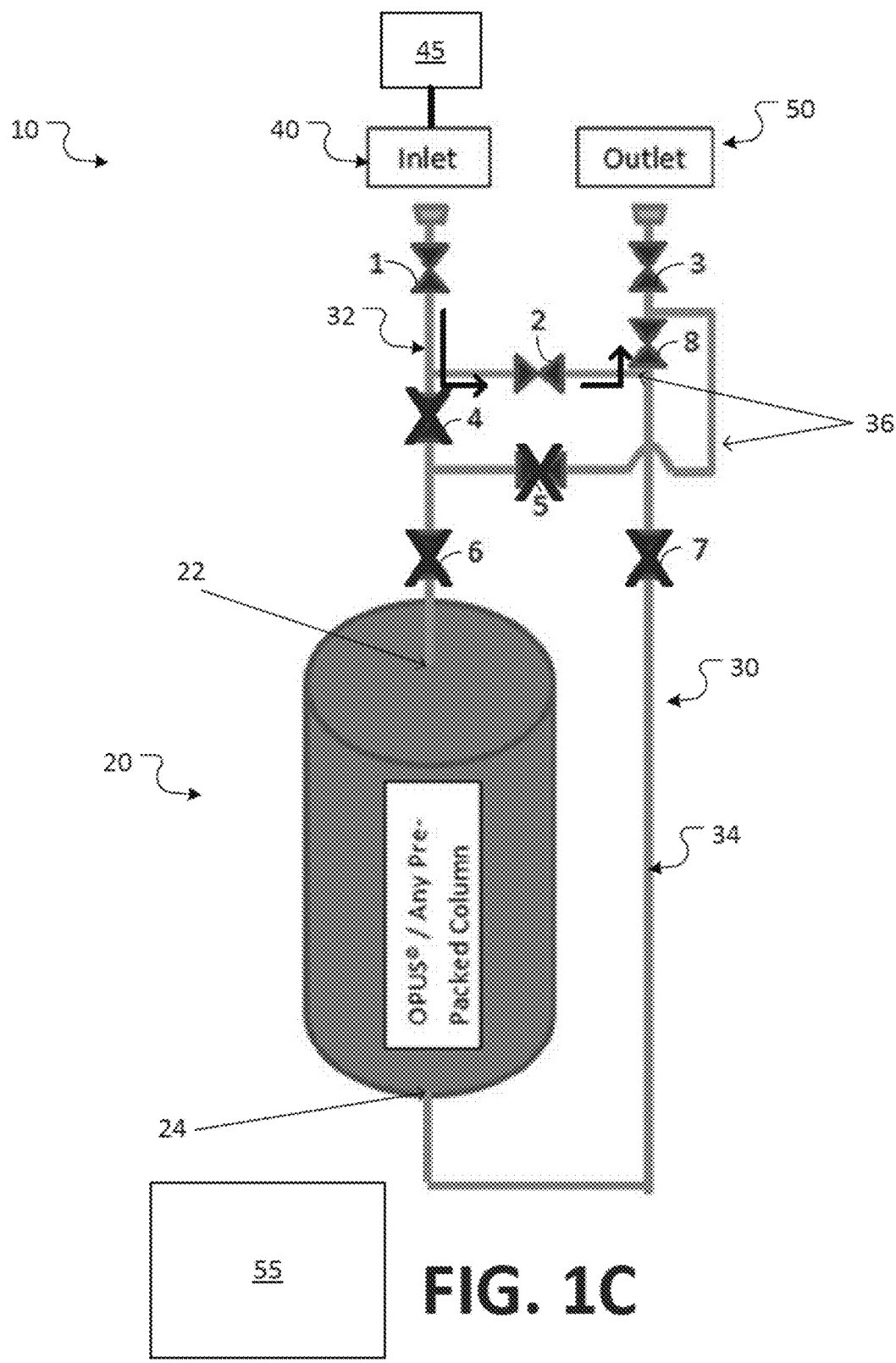

A second priming sequence is shown in FIG. 1C. This sequence primes the top portion of the tubing and valve set 30, e.g., the portions of the tubing and valve set 30 closest to the fluid inlet 40 and the fluid outlet 50. In this instance, valves 1, 2, 3, and 8 are open while valves 4, 5, 6, and 7 are closed. Fluid downflow proceeds from the inlet and then exits out of the fluid outlet 50 via the upper branch 36. Fluid flow is controlled to continue at least until the portion of the tubing nearest valve 8 is filled with fluid.

Figure 1D:
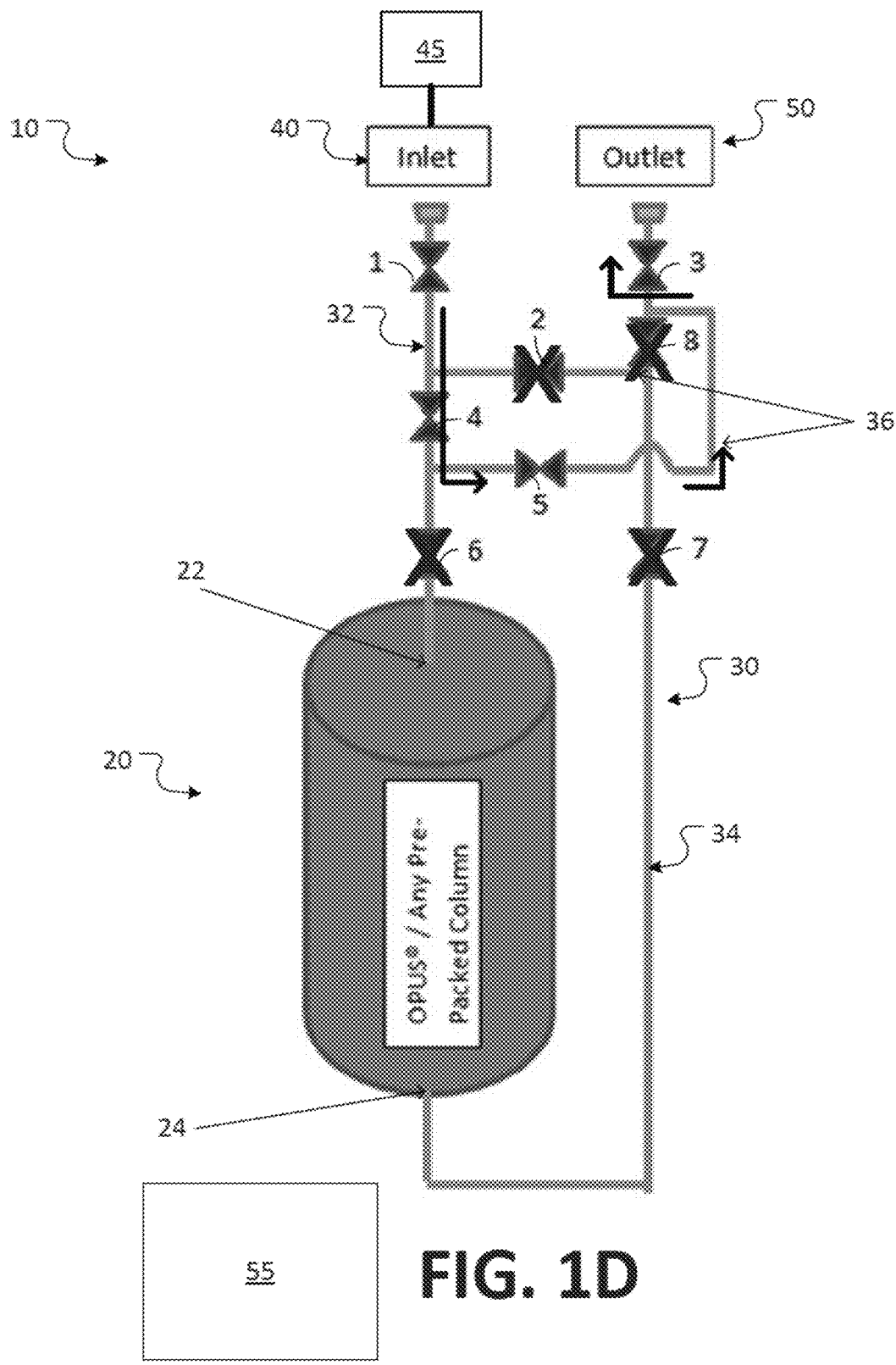

A third priming sequence is shown in FIG. 1D. This sequence primes the remaining portion of the tubing and valve set 30, e.g., the portion of the tubing and valve set 30 closest to valve 4. In this instance valves 1, 3, 4, and 5 are open while valves 2, 6, 7, and 8 are closed. Fluid downflow proceeds from the inlet 40 and along upstream tubing 32 including valve 4 to tubing branch 36 with valve 5, then to the latter portion of downstream tubing 34 to fluid outlet. Fluid flow is controlled to continue at least until the portion of the tubing nearest valve 5 is filled with fluid.

In some instances, and because it is likely that post-gamma irradiation there are air bubbles and/or pressure in the upper portions of the tubing set, the priming steps of FIGS. 1C and 1D are performed first and second in a post-gamma irradiated column, before any flow through the column. Doing so ensures no further air will enter the column. In various scenarios, the priming step of FIG. 1D can come before the priming step of FIG. 1C, and vice versa. In general, the priming steps of FIGS. 1C and 1D can be carried out in any order before FIG. 1B, as long as no air enters the column in the downflow.

Figure 1E:
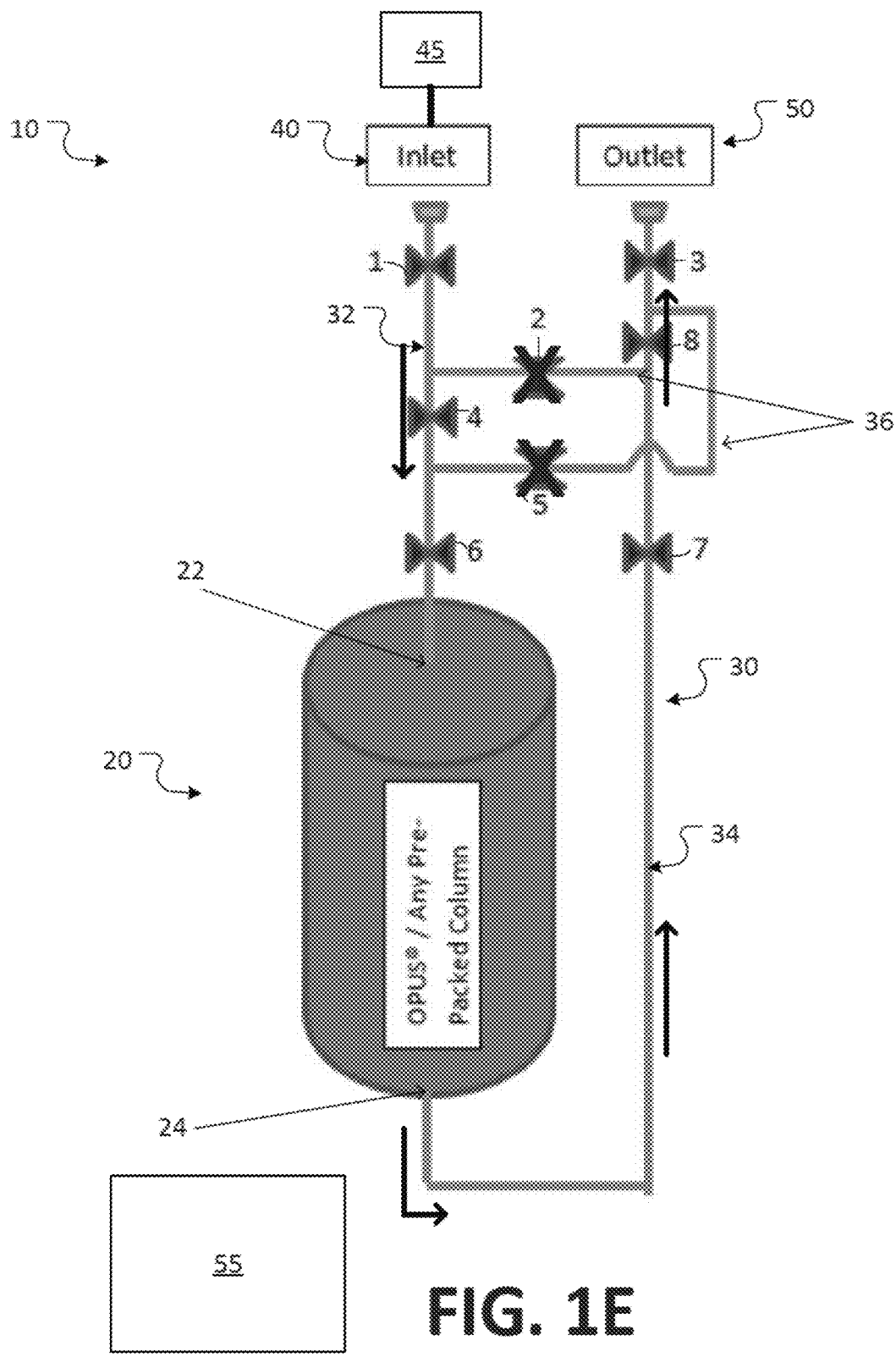

A fourth priming sequence is shown in FIG. 1E. This sequence primes the downstream portion of the tube 34. This configuration is also used for downflow operation using the tubing and valve set 30. Here, valves 1, 3, 4, 6, 7, and 8 are open while valves 2 and 5 are closed. With this valve set up, downflow operation is achieved by downflow from inlet 40 and the solution will exit from the fluid outlet 50 as shown by the arrows.

After the priming sequences shown in FIGS. 1B-E are completed (FIG. 1B shows an upflow sequence and FIG. 1E shows a downflow sequence), the tubing and valve set 30 and the column 20 are completely filled with liquid and ready for chromatography operations, with any bubbles and/or pressure that may have been present being removed. Any air remaining in the outlet portion 34 will be removed by the downflow. The system 10 can also be used for upflow operation while using the tubing set.

For upflow operation valves 1, 2, 3, 6, and 7 are open while valves 4 and 8 are closed. This configuration allows the same fluid flow path as shown in FIG. 1B for upflow conditioning of the column. In both the system of FIG. 1A and 2B upflow occurs without additional changes such as flipping the column upside down, or making other changes to the system such as reversing the direction of the pump 45 that propels fluid from fluid inlet 40 to fluid outlet 50. In addition, this upflow sequence does not need the column to be physically re-plumbed, thereby maintaining the aseptic/sterile nature of the column and tubing and valve set, e.g., if the column was gamma irradiated.

Figure 2A:
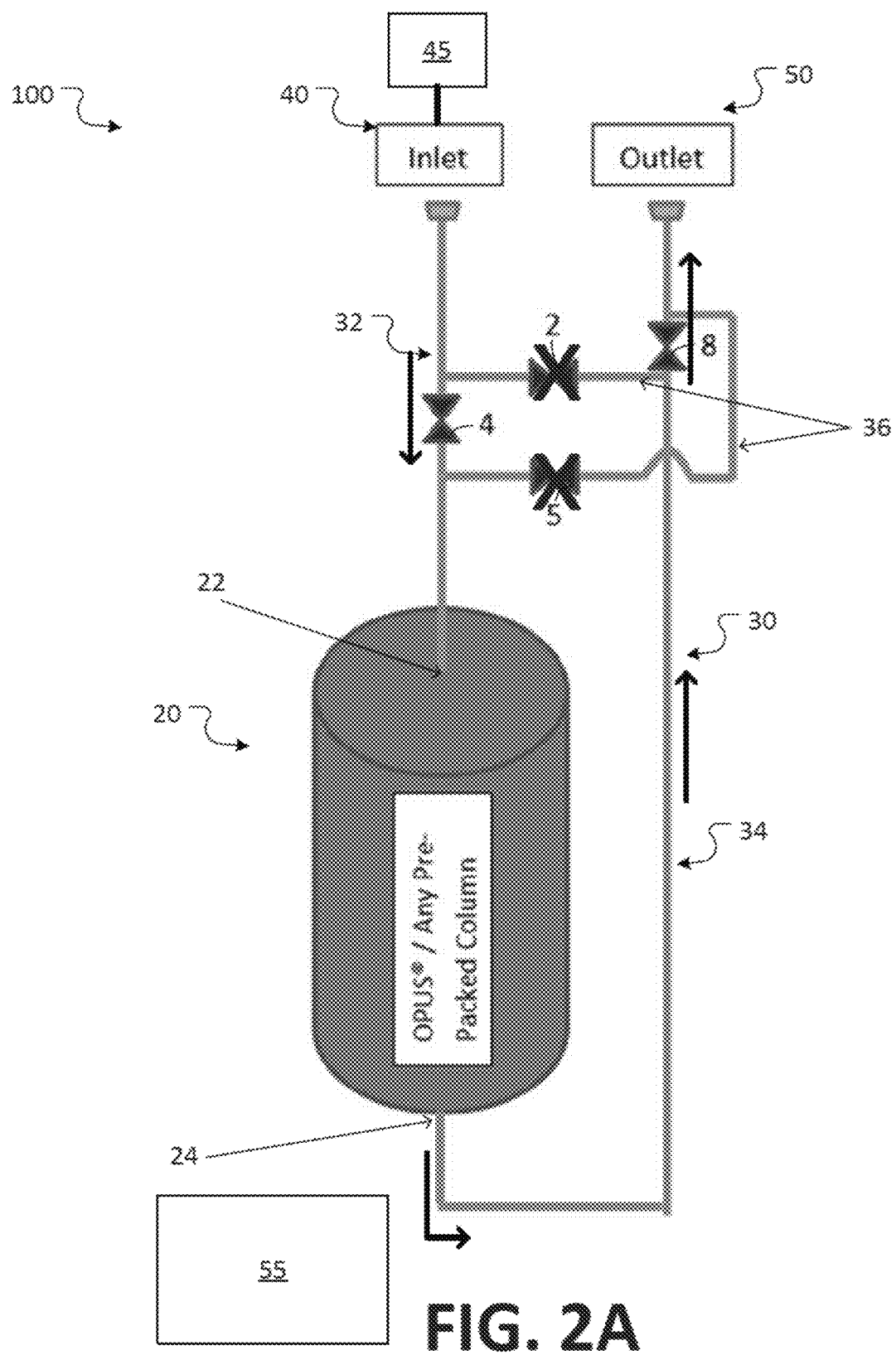
FIG. 2A and B are schematic diagrams of another embodiment of a sterile or aseptic chromatography column and associated system of valves and tubing forming fluid flow paths of a closed system connected to the column, a described herein.
Figure 2B:
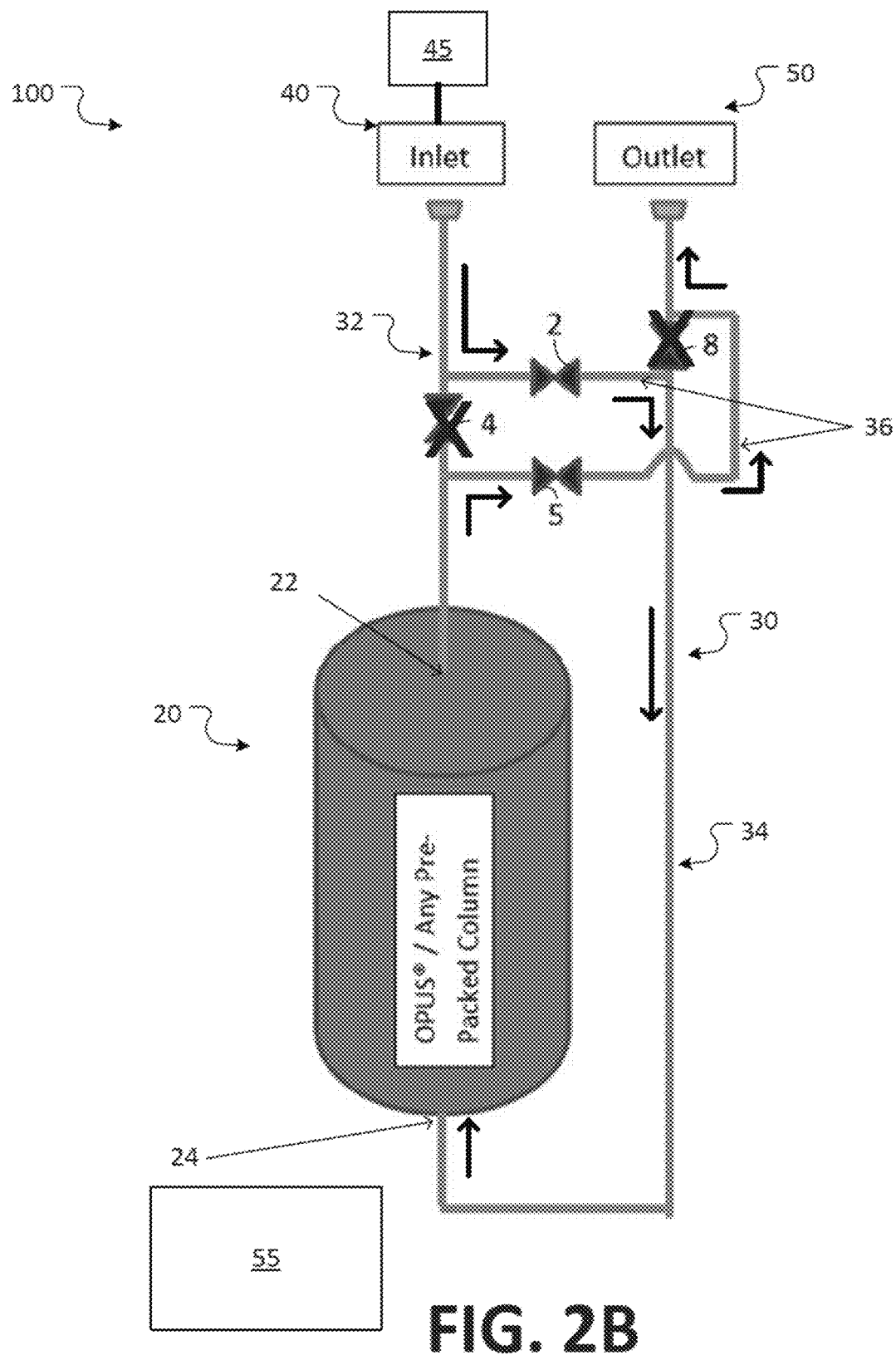

Referring to FIG. 2A, a second embodiment of a sterile or aseptic chromatography column system 100 is shown. The components of the sterile or aseptic chromatography column system 100 are similar to those of FIGS. 1 and the same reference numbers refer to the same system elements. The embodiment in FIG. 2A has a similar flow path as shown as in FIG. 1A, but includes only valves 2, 4, 5, and 8. When in downflow operative use, valves 2 and 5 are closed (as indicated by the X on each valve in the figure) and the fluid path is as shown by the arrows. Referring to FIG. 2B, when in upflow operative use, valves 4 and 8 are closed (as indicated by the X on each valve in the figure) and the fluid path is as shown by the arrows.

Figure 3A:
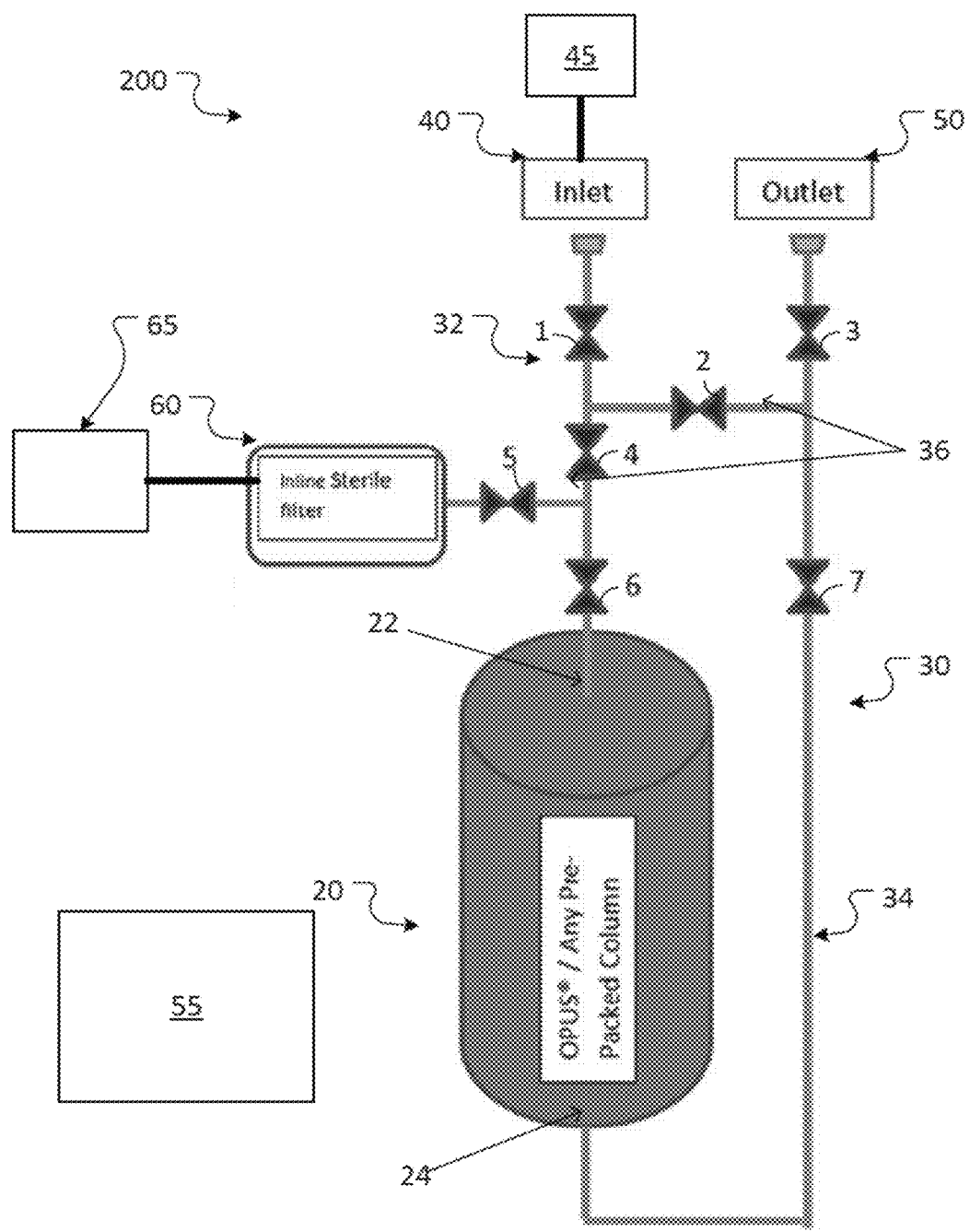
FIGS. 3A-E are schematic diagrams of another embodiment of a sterile or aseptic chromatography column and associated system of valves and tubing to form fluid flow paths of a closed system connected to the column, as described herein.

In some embodiments, fluid exiting the column 20 does not flow out of the fluid outlet 50. FIG. 3A shows a sterile or aseptic chromatography column system 200 similar to the previous embodiments and with the same elements numbered with the same reference numbers. However, the tubing and valve set includes only valves 1-7 and the tubing branch 36 that includes valve 5 does not connect the upstream tubing 32 to the downstream tubing 34. Instead, that tubing branch 36 is fluidly connected to the upstream tubing 32 on one end and to an inline sterile or aseptic filter 60 at the second end. The inline sterile or aseptic filter 60 can be used as an outlet to prime the tubing and valve set 30 rather than fluid outlet 50. In some embodiments, inline sterile or aseptic filter 60 can be connected to a fluid collection container 65. Fluid collected in the fluid collection container 65 can be used for testing purposes, e.g., to determine the condition or properties of the fluid and/or resin within the column 20.

Figure 3B:
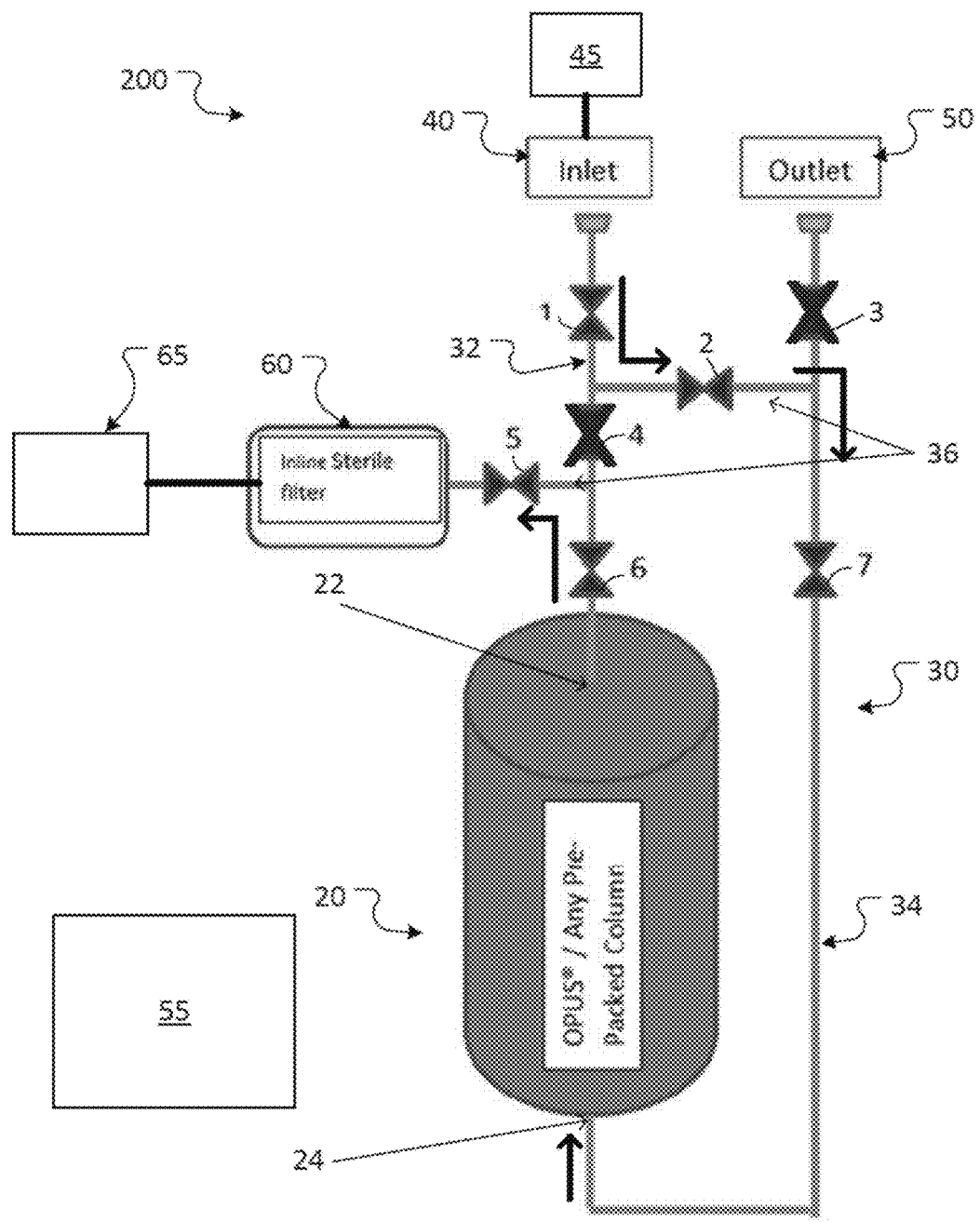

The sterile or aseptic chromatography column system 200 of FIG. 3A can be used to prime the chromatography column 20 while, e.g., removing any gas bubbles and/or pressure that might be present in the column 20, the tubing 30, and any connectors such as the column inlet 22 and column outlet 24. A first priming sequence for system 200 is shown in FIG. 3B. Valves 1, 2, 5, 6, and 7 are open, as indicated, while valves 3 and 4 are closed. This configuration permits liquid downflow of the upstream tubing 32 and upflow conditioning of the column 20. Typically, three or more column volumes (CVs) of fluid are pumped through the column. As shown by the arrows in FIG. 3B, fluid proceeds from fluid inlet 40 along the upstream tubing 32 through connective tubing branch 36 to the downstream tubing 32, and then from column outlet 24 through the column 20 and out from column inlet 22. Due to valve 4 being closed the fluid then is diverted along the tubing branch 36 to the inline sterile or aseptic filter 60 and optionally to a collection container 65.

Figure 3C:
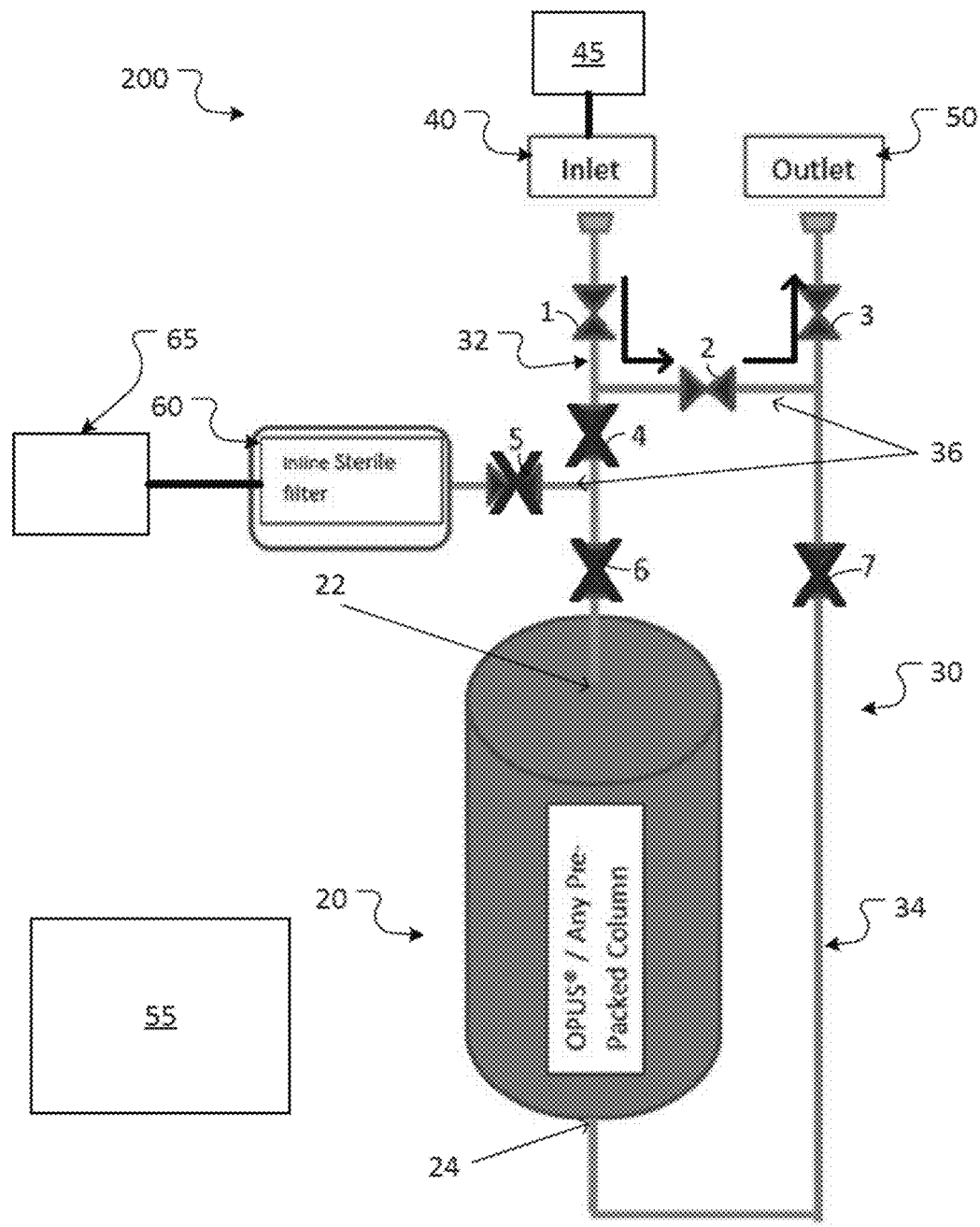

A second priming sequence is shown in FIG. 3C. This sequence primes the top portion of the tubing and valve set 30, e.g., the portions of the tubing and valve set 30 closest to the fluid inlet 40 and the fluid outlet 50. In this instance, valves 1, 2, and 3 are open while valves 4, 5, 6, and 7 are closed (or alternatively only valves 4 and 7 are closed). Fluid downflow proceeds from the fluid inlet 40, across the tubing branch 36 with valve 2 and then exits out of the fluid outlet 50. Fluid is controlled to continue to flow at least until the portion of the tubing including valve 2 is filled with fluid.

Figure 3D:
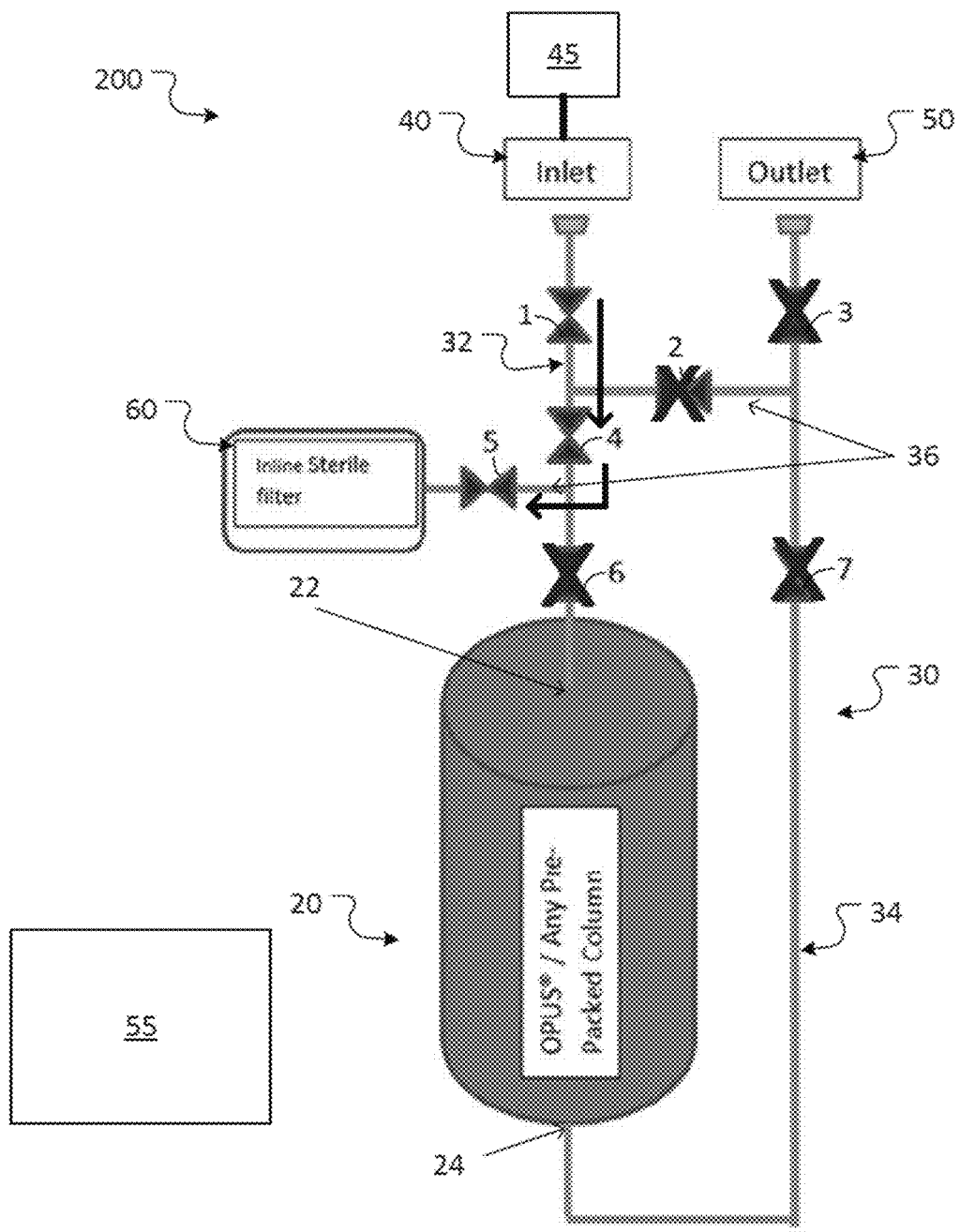

A third priming sequence is shown in FIG. 3D. This sequence primes the remaining portion of the tubing set 30, e.g., the portion of the tubing set 30 closest to valve 4. In this instance valves 1, 4, and 5 are open while valves 2, 3, 6, and 7 are closed. Fluid downflow proceeds from the inlet 40 and along upstream tubing 32 including valve 4 to tubing branch 36 with valve 5, and out to the inline sterile or aseptic filter 60. Fluid flows at least until the portion of the tubing nearest valve 4 is filled with fluid. In some instances, the priming steps of FIGS. 3C and 3D are performed first and second in a post-gamma irradiated column, before any flow through the column. Doing so ensures no further air will enter the column. These steps can also be reversed.

Figure 3E:
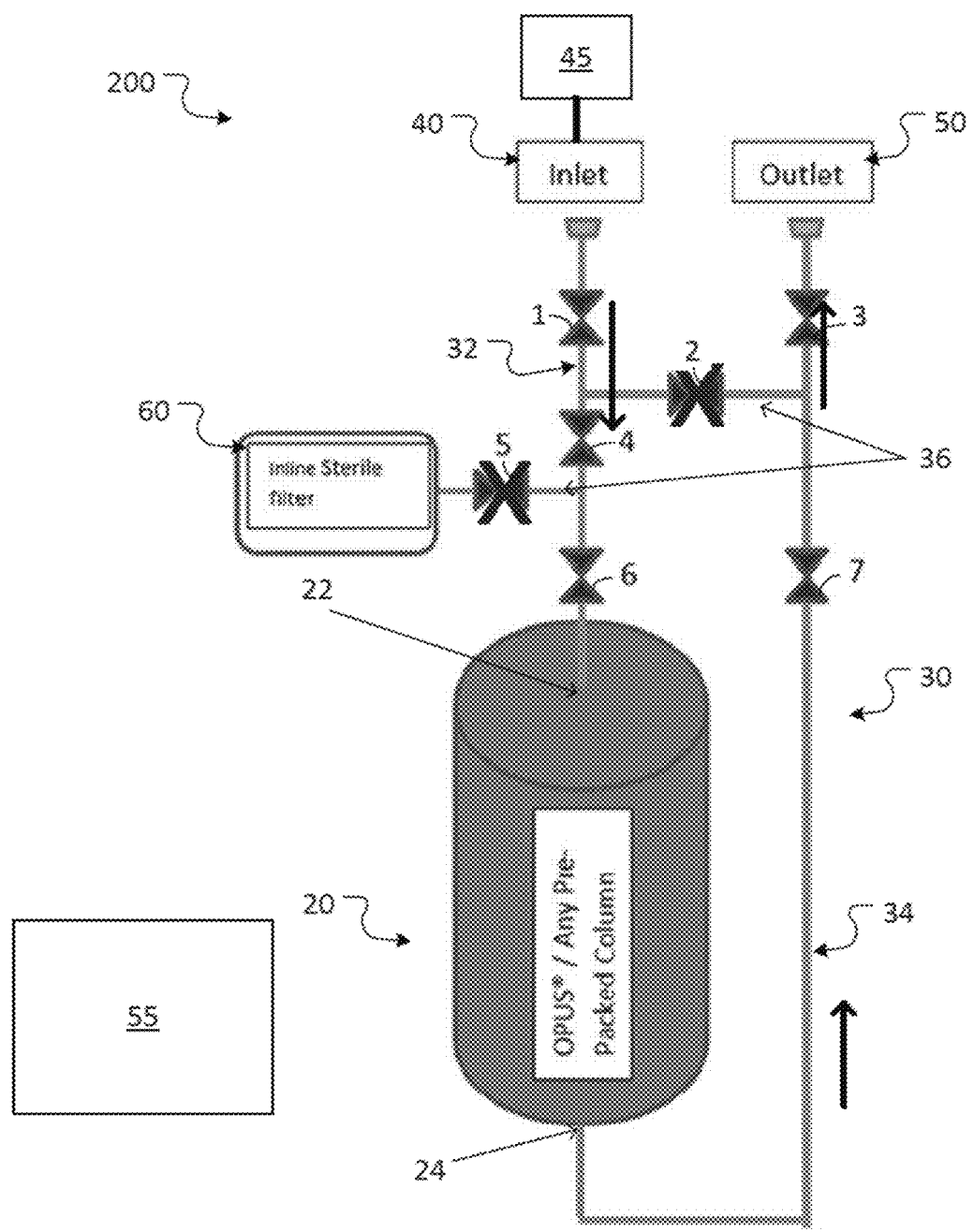

After the priming sequences shown in FIGS. 3B-D, the tubing and valve set 30 and the column 20 are completely filled with liquid and ready for chromatography operations. A configuration for a downflow operation using the tubing set 30 is shown in FIG. 3E. Here, valves 1, 3, 4, 6, and 7 are open while valves 2 and 5 are closed. With this valve set up, downflow operation is achieved by downflow from inlet 40 and solution will exit out of the fluid outlet 50 as shown by the arrows while traversing the column 20.

Figure 4:
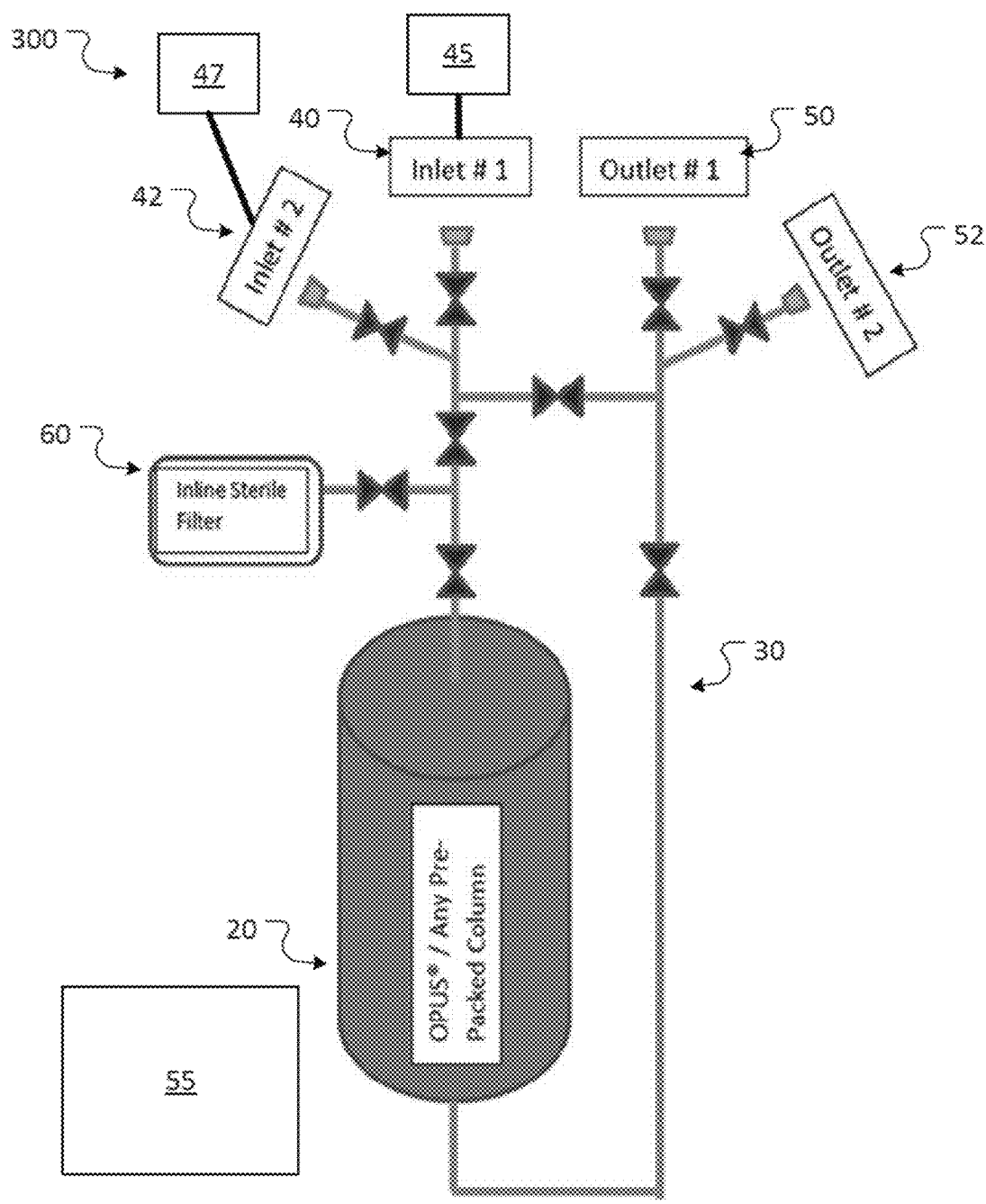
FIG. 4 is a schematic diagram of an embodiment of a sterile or aseptic chromatography column and system of valves and tubing forming a closed system.

FIG. 4 shows an additional sterile or aseptic chromatography column system 300. In addition to the elements that are the same as discussed in the embodiments above, system 300 includes a second fluid inlet 42 and a second fluid outlet 52, with associated additional valves. Various fluid sources and sinks are therefore possible, in addition to the optional fluid container connected to inline sterile or aseptic filter 60. A second pump 47 is shown connected to second fluid inlet 42, however in system 300 as in all sterile or aseptic systems described herein, more than one or two flow pumps are possible. In some instances, one or more pumps are used, such that an operator can use one set of the inlet and outlet connectors and pre-prime the tubing set and column to remove all the air and then clamp off those tubing. Afterwards, the column can be used on a later date without priming the column again. In addition, because there is still one set of unused sterile or aseptic connectors, the column can be hooked up under sterile or aseptic or aseptic conditions again. Alternatively, an operator can use the two sets of sterile or aseptic connections to use the column twice.

Figure 5:
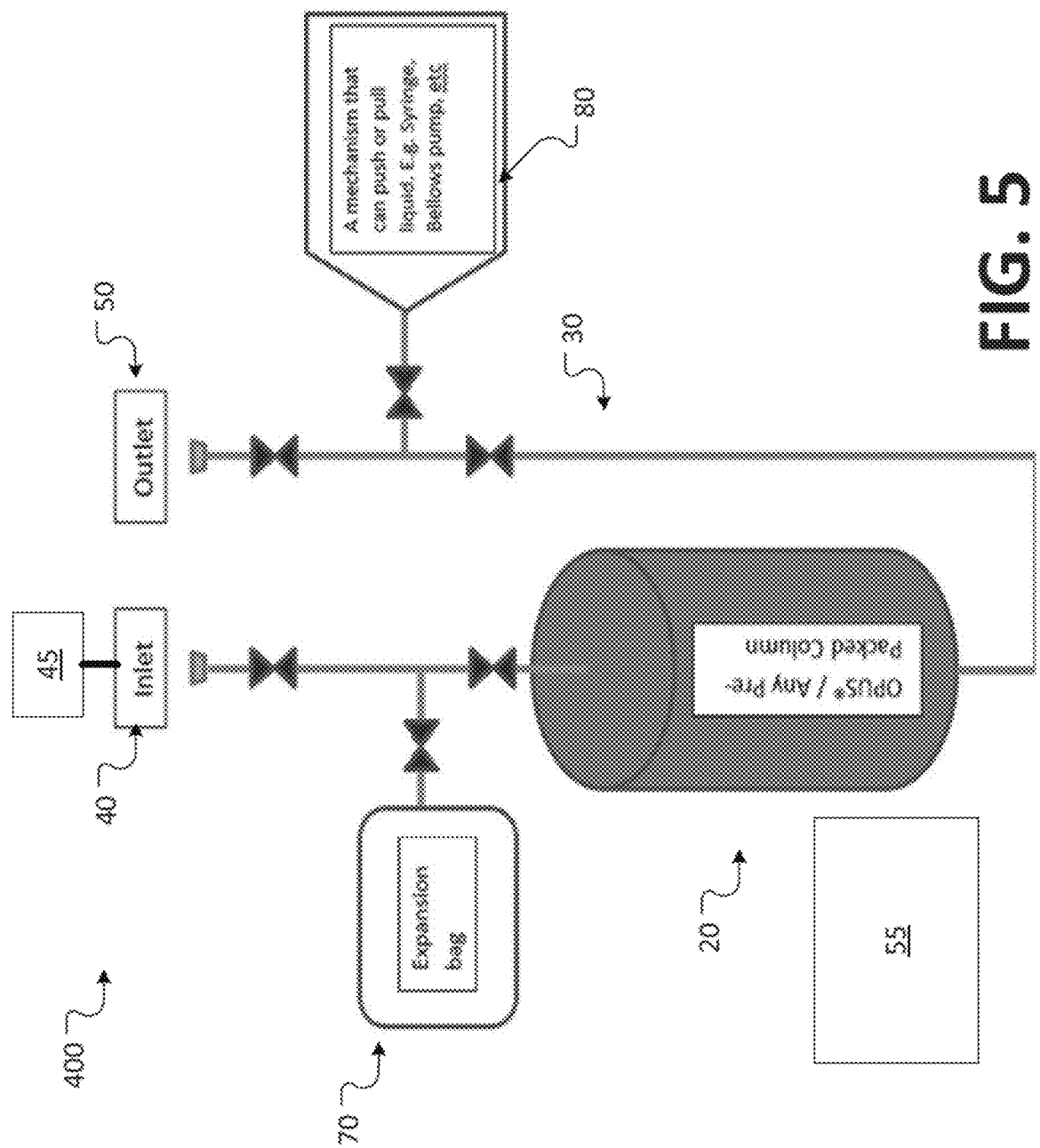
FIG. 5 is a schematic diagram of an embodiment of a sterile or aseptic chromatography column and system of valves and tubing forming a closed system.

FIG. 5 shows an additional sterile or aseptic chromatography column system 400. In addition to the elements that are the same as discussed in the embodiments above, system 400 includes an expansion bag 70. The expansion bag 70 can be partially filled with buffer. The expansion bag 70 can optionally include a vent external to system 400 that includes a sterile or aseptic filter. Sterile or aseptic chromatography column system 400 also can include a secondary pump 80. The secondary pump 80 is fluidly connected to the tubing and valve system 30 and can push or pull liquid through the tubing 30, in addition to the in-place pumping system 45. The secondary pump can be manual, e.g., a syringe, or bellows pump. Rather than redirecting fluid through use of valves, the secondary pump 80 can direct fluid upflow if desired.

Figure 6:
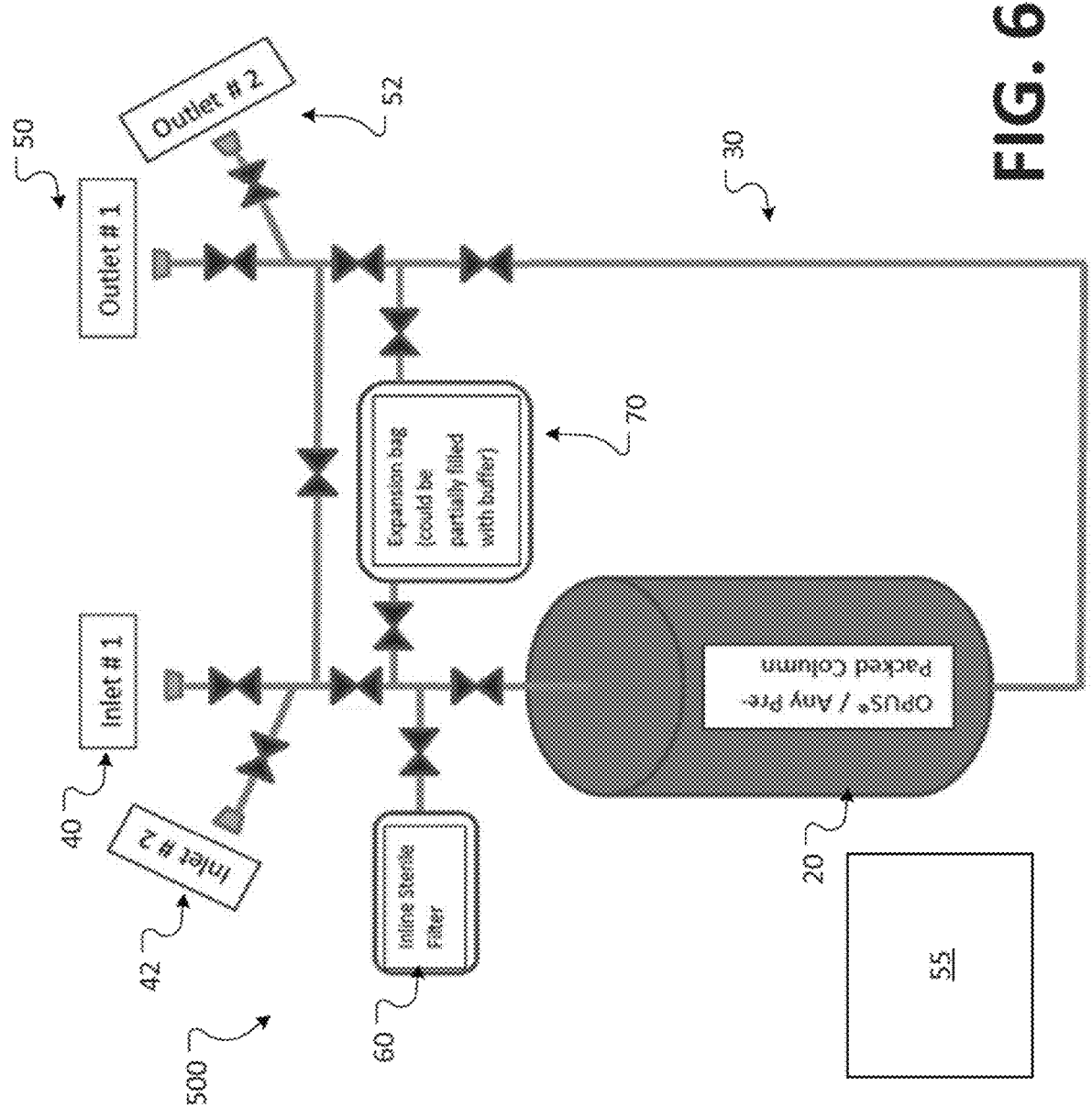
FIG. 6 is a schematic diagram of an embodiment of a sterile or aseptic chromatography column and system of valves and tubing forming a closed system.

FIG. 6 shows an additional sterile or aseptic chromatography column system 500. In addition to the elements that are the same as discussed above with respect to FIG. 1A, the system 500 includes the features of the embodiments of FIGS. 4 and 5. These features include a second fluid inlet 42 and a second fluid outlet 52, an expansion bag 70, and a sterile or aseptic filter 60. Additional valves connect the various tubing elements and controller 55 can direct fluid to all these elements.

Figure 7:
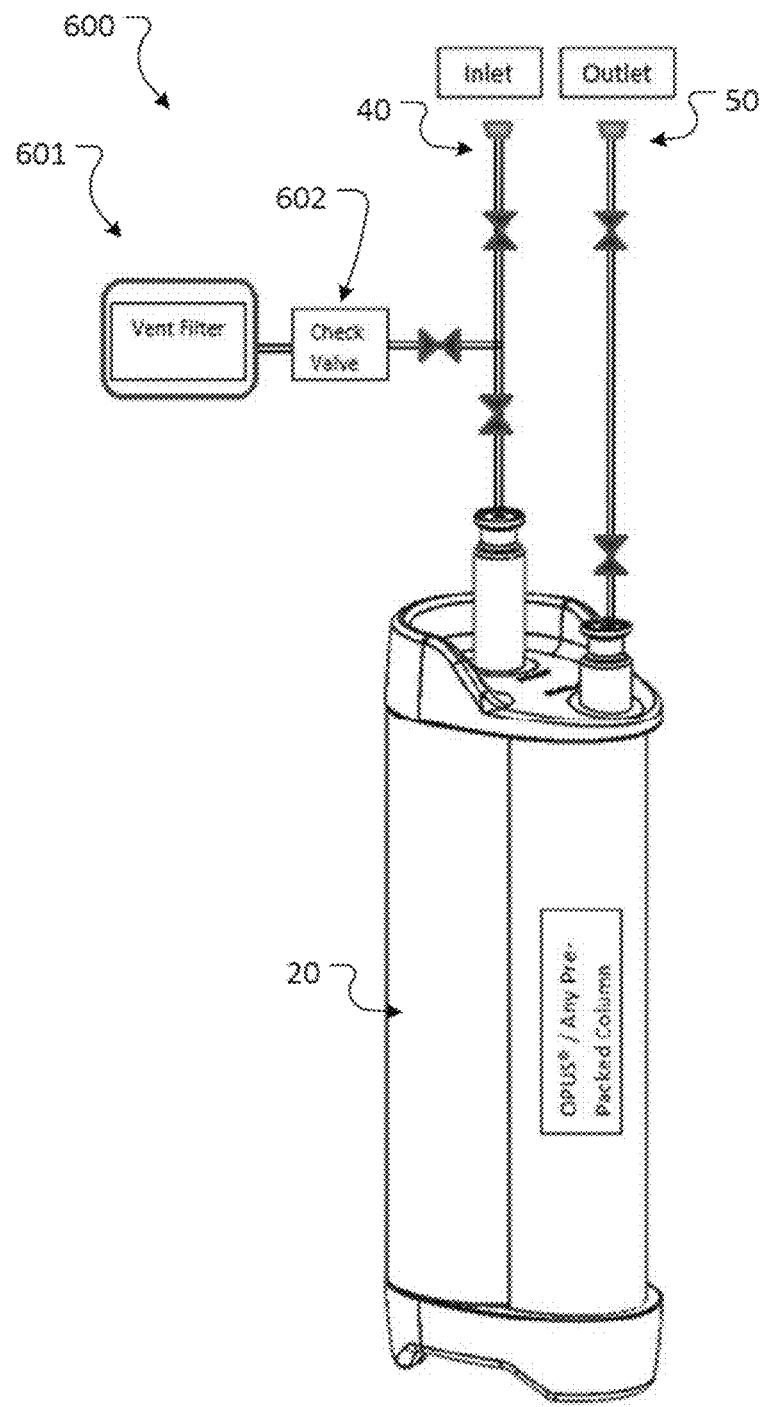
FIG. 7 is a schematic diagram of an embodiment of a sterile or aseptic chromatography column and system of valves and tubing for a closed system.

FIG. 7 shows an additional sterile or aseptic chromatography column system 600. In addition to the elements that are the same as discussed above with respect to FIG. 1A, the system 600 includes a sterilizing grade hydrophobic vent filter 601 incorporated to relieve pressure build up or to evacuate trapped gasses. The hydrophobic vent filter 601 in combination with a check valve 602 ensures venting in one direction without backflow into the system 600.

Figure 8:
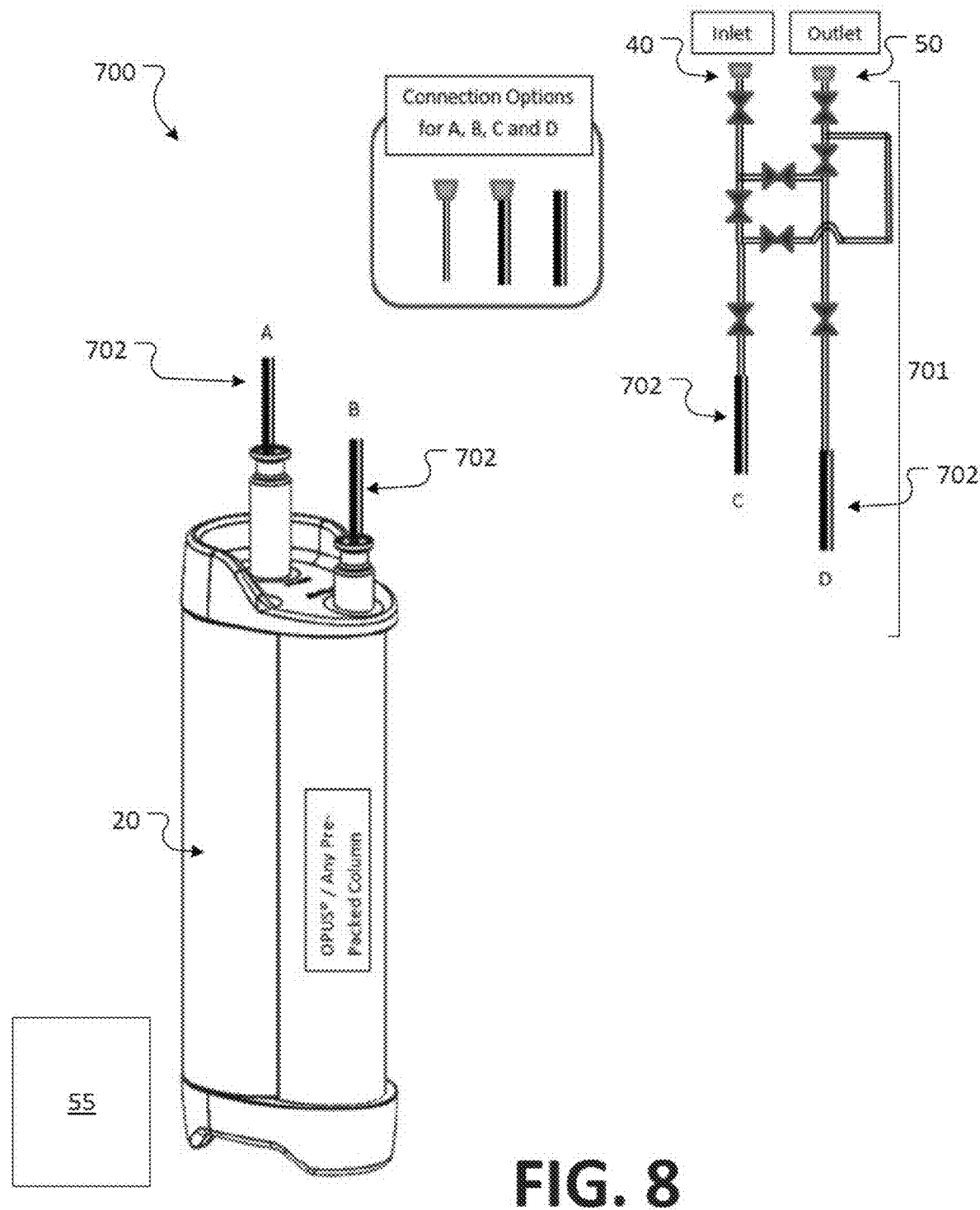
FIG. 8 is a schematic diagram of an embodiment of a sterile or aseptic chromatography column and system of valves and tubing for a closed system.

FIG. 8 shows an additional sterile or aseptic chromatography column system 700. In addition to the elements that are the same as discussed above with respect to FIG. 1A, the system 700 includes a tubing set 701 and column 20 that include weldable tubing or sterile or aseptic connections A, B, C, D that allow the tubing set and column to be connected independently, and in a sterile or aseptic manner, after the gamma irradiation. The column 20 and tubing set 701 can be gamma irradiated separately as long as a method of sterile or aseptically connecting the two parts post-gamma irradiation is available. FIG. 7 illustrates weld-able tubing 702 present on the column 20 and tubing set 701. A sterile or aseptic connection can be welded (A to C and B to D) between the weld-able tubing 702 or can be made through sterile or aseptic connectors (not shown). The post-gamma sterile or aseptic attachment of a tubing set 701 to a chromatography column 20 can be applied to any tubing set 701, provided a method of sterilely or aseptically connecting the two parts post-gamma irradiation is available.

EXAMPLES

The following examples illustrate, but do not limit, the systems and methods described herein.

Example 1

Evaluation of Tubing Set and Priming Sequences

During the process of gamma irradiation gasses and pressurization occurs within the closed column, which can negatively affect column usability. Through a tubing and valve set, these gasses and pressure can be removed from the column as described herein. The goal of this experiment was to demonstrate air removal efficiency for tubing and valve set 30. Two pre-packed OPUS® columns (Repligen Corporation) were used. Each pre-packed column had dimensions of 10 cm inner diameter and a 20 cm bed height packed with GE Healthcare Capto™ S, an agarose based cation exchange resin. For this experiment, the tubing set was not primed and (full of air) to demonstrate a worst-case scenario to model effects of gamma processing.

Figure 9B:
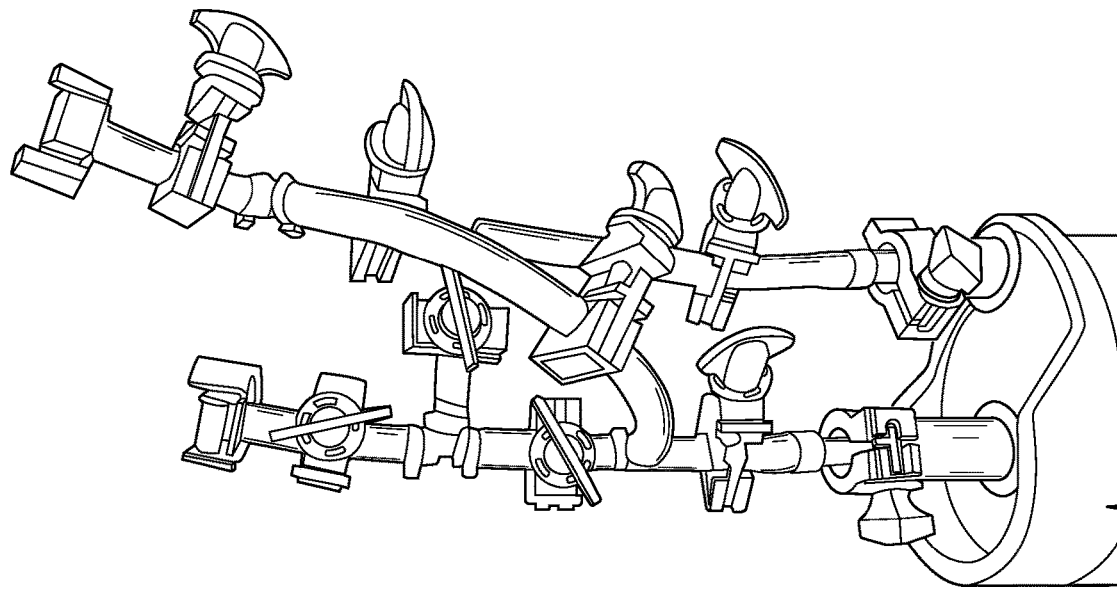
FIGS. 9A-D are representations of an example of an experimental unit for testing the column of FIG. 1A.
Figure 9A:
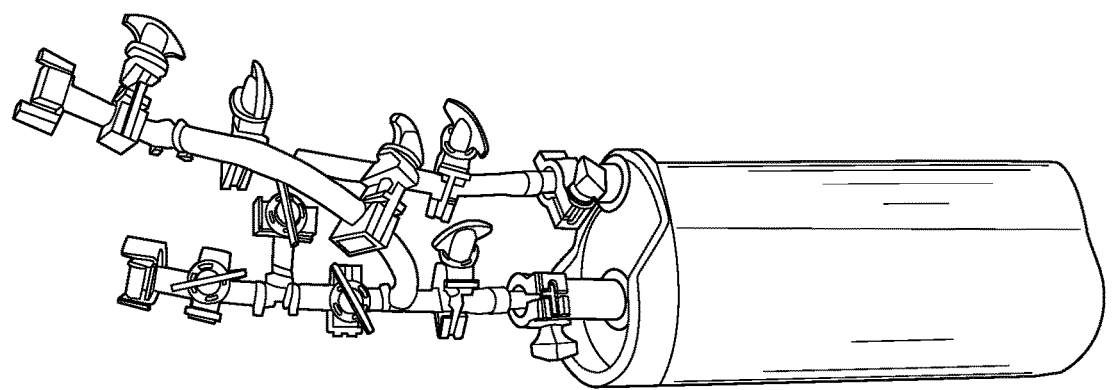
Figure 9D:
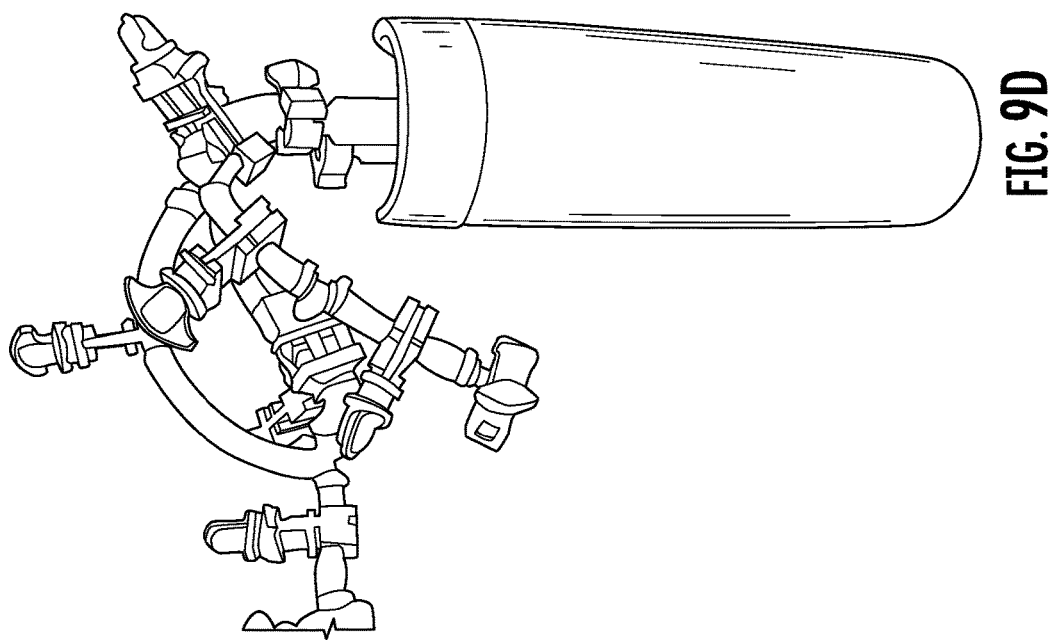

The columns with tubing sets were connected to an AKTApilot® (FIG. 9D). The tubing set was primed with the following sequence:

Step 1: Valves 1, 2, 8, and 3 open and valves 4, 5, 6, and 7 closed.

Step 2: Valves 1, 4, 5, and 3 open and valves 2, 6, 7, and 8 closed.

Step 3: Upflow operation sequence (e.g., forward direction of pump)—valves 1, 2, 7, 6, 5, and 3 open and valves 4 and 8 closed.

Step 4: Downflow operation sequence—valves 1, 4, 6, 7, 8, and 3 open and valves 2 and 5 closed.

Several observations were made during the process. The first two sequences primed the majority of the tubing set. The upflow sequence primed the inlet line while not introducing air into the bottom of the column due to the outlet line that is positioned at the same height as the inlet line, which is located at the top of the column. The downflow sequence primed the outlet and the last leg of the tubing set.

In conclusion, after the priming sequence was completed, the tubing set did not contain any entrapped air as determined by visually inspection. The valve combination set-up was demonstrated to be functional in removing air from the columns and tubing system via described methods.

Example 2

Removal of Air Post-Gamma Irradiation and Column Performance Testing

The following experiment was carried out to evaluate the sterile or aseptic chromatography column system shown in FIG. 1A to confirm that this embodiment can fully prime and remove trapped air in the tubing set 30 post gamma irradiation.

Additionally, the test was carried out to confirm the valve combination set-up for priming upflow and downflow operations, and to determine that the addition of the tubing and valve set 30 does not affect column performance.

The two pre-packed columns used in Example 1 were also used for this experiment. These two columns were tested on an AKTApilot® chromatography system (GE Healthcare) for HETP (N/m) and asymmetry with and without tubing set prior to gamma sterilization. The columns were tested at 100 cm/hr in 100 mM NaCl with a 1% CV 1 M NaCl spike injection. The addition of the tubing set did not affect the column performances of these columns (Table #1).

Figure 9C:
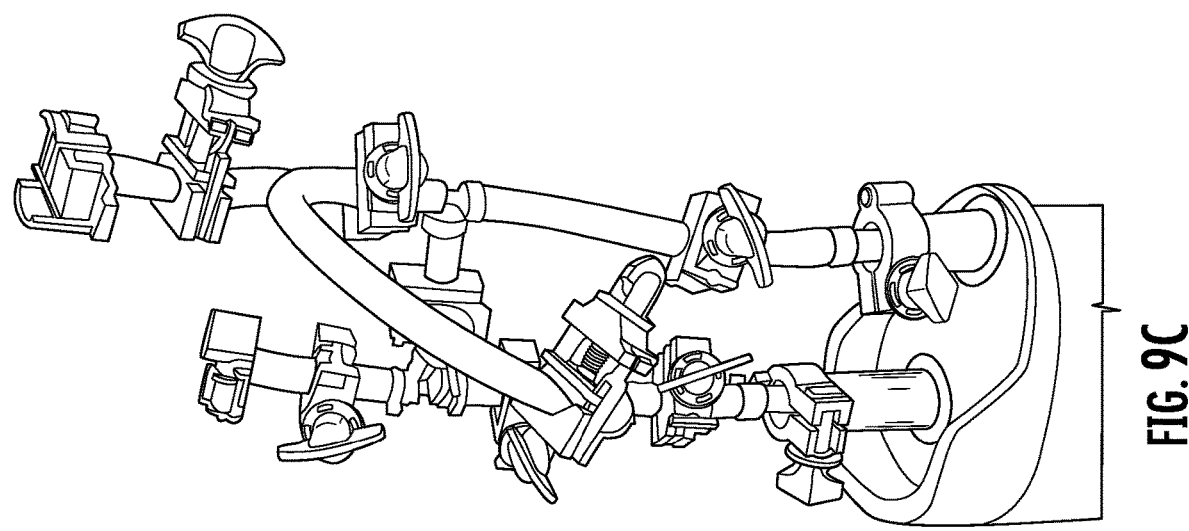

FIGS. 9A-C shown the tubing and valve set 30 attached to an OPUS® 10 cm inner diameter column. FIG. 9D shows the tubing and valve set 30 attached to an AKTApilot®.

In preparation for gamma irradiation, each tubing set and pre-packed column assembly was primed and stored with phosphate buffered saline (PBS) containing 2% Benzyl Alcohol. No air was observed in the tubing assembly after storage and prior to gamma irradiation.

The columns were gamma irradiated to a target range of 25-40 Gy.

Post-gamma sterilization, entrapped air was observed within each tubing set assembly in the following locations:

Air bubbles observed at locations:

between valve 1 and 4 between valve 7 and 8 below valve 6

Both columns were tested post-gamma irradiation for column performance.

The tubing set was primed with 100 mM NaCl at a flow rate of 100 cm/hour.

Priming Sequence:

Step 1: Valves 1, 2, 8, and 3 open and valves 4, 5, 6, and 7 closed.

Step 2: Valves 1, 4, 5, and 3 open and valves 2, 6, 7, and 8 closed.

Step 3: Downflow sequence—valves 1, 4, 6, 7, 8, and 3 open and valves 2 and 5 closed.

Air was observed to be removed from column outlet 24 during the downflow sequence. Both columns were tested and decreased HETP (N/m) were observed for both columns when compared to before gamma irradiation. Asymmetry was tailing more for column #1 post-gamma irradiation (Table 1).

An upflow sequence was then performed (valves 1, 2, 7, 6, 5, and 3 open and valves 4 and 8 closed) on both columns with tubing sets and air was observed to exit the inlet of the column. The columns were tested, which resulted in improved HETP (N/m) for both columns and improved asymmetry for column #1 when compared to the initial post-gamma irradiation test.

TABLE 1

| Capto™ S | Initial test without tubing set | Retest before gamma without tubing set | Testing with Tubing Set of FIG. 1 before gamma | Post Gamma - Priming of tubing set only (no upflow on column) | Post Gamma- After 1 CV upflow with tubing set |
|---|---|---|---|---|---|
| Column # 1 HETIP (N/m): | 3351 | 3631 | 3649 | 3337 | 3606 |
| (10 × 20 cm) Asym: | 1.02 | 1.03 | 1.08 | 1.53 | 0.98 |
| Column # 2 HETP (N/m): | 3725 | 3709 | 3624 | 3402 | 3806 |
| (10 × 20 cm) Asym: | 0.94 | 0.97 | 1.05 | 0.97 | 0.97 |

Figure 10A:
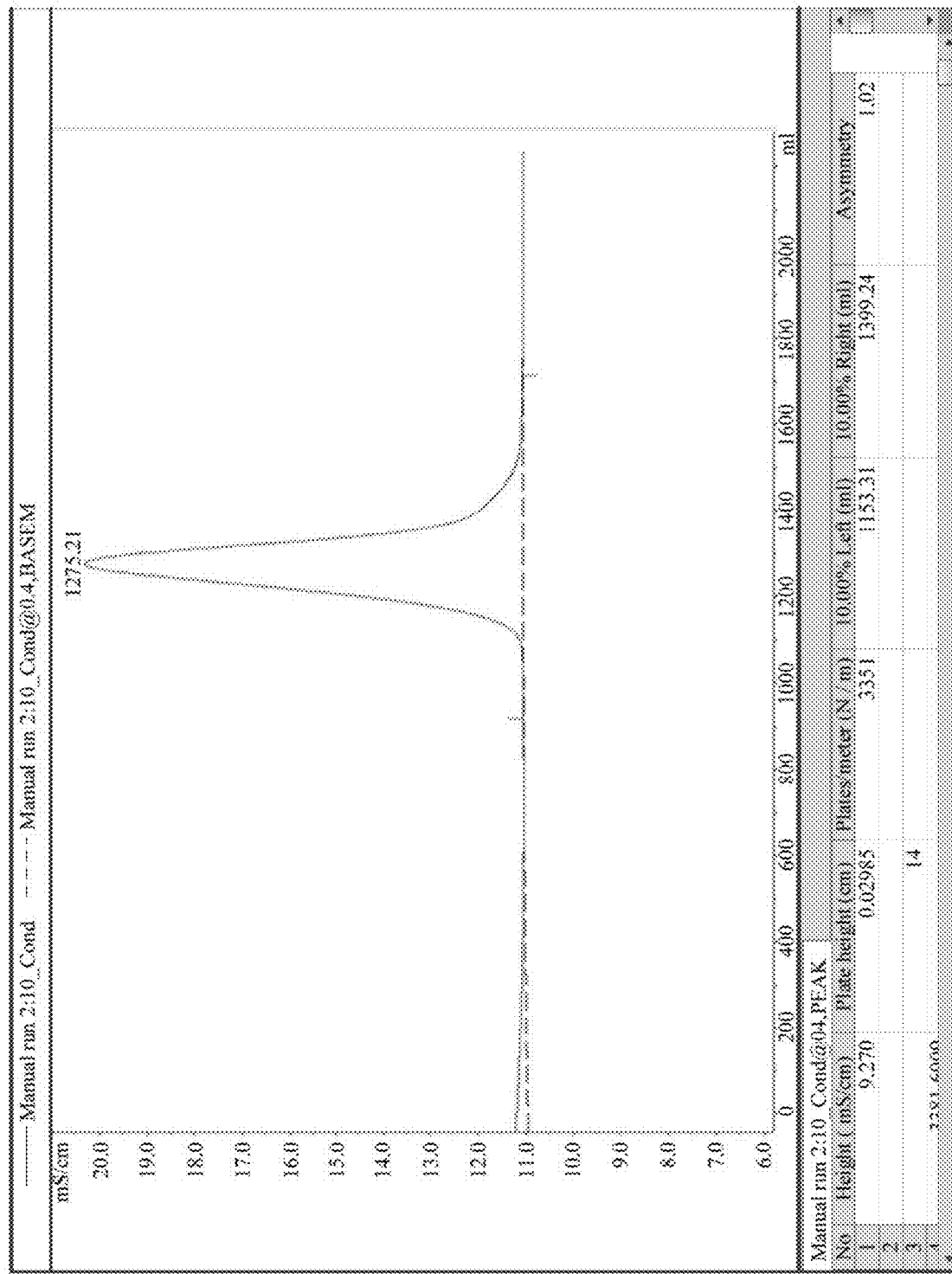
FIGS. 10A-J are chromatograms showing experimental data of Table 1.

In conclusion, the tubing and valve set successfully removed air bubbles found in the tubing set post-gamma irradiation. Furthermore, the tubing and valve set also helped recover lost HETP (N/m) through upflow operation. The following figures show the following results:

FIG. 10A shows the results of the Capto™ S Column #1 (10×20 cm) initial test after packing.

Figure 10B:
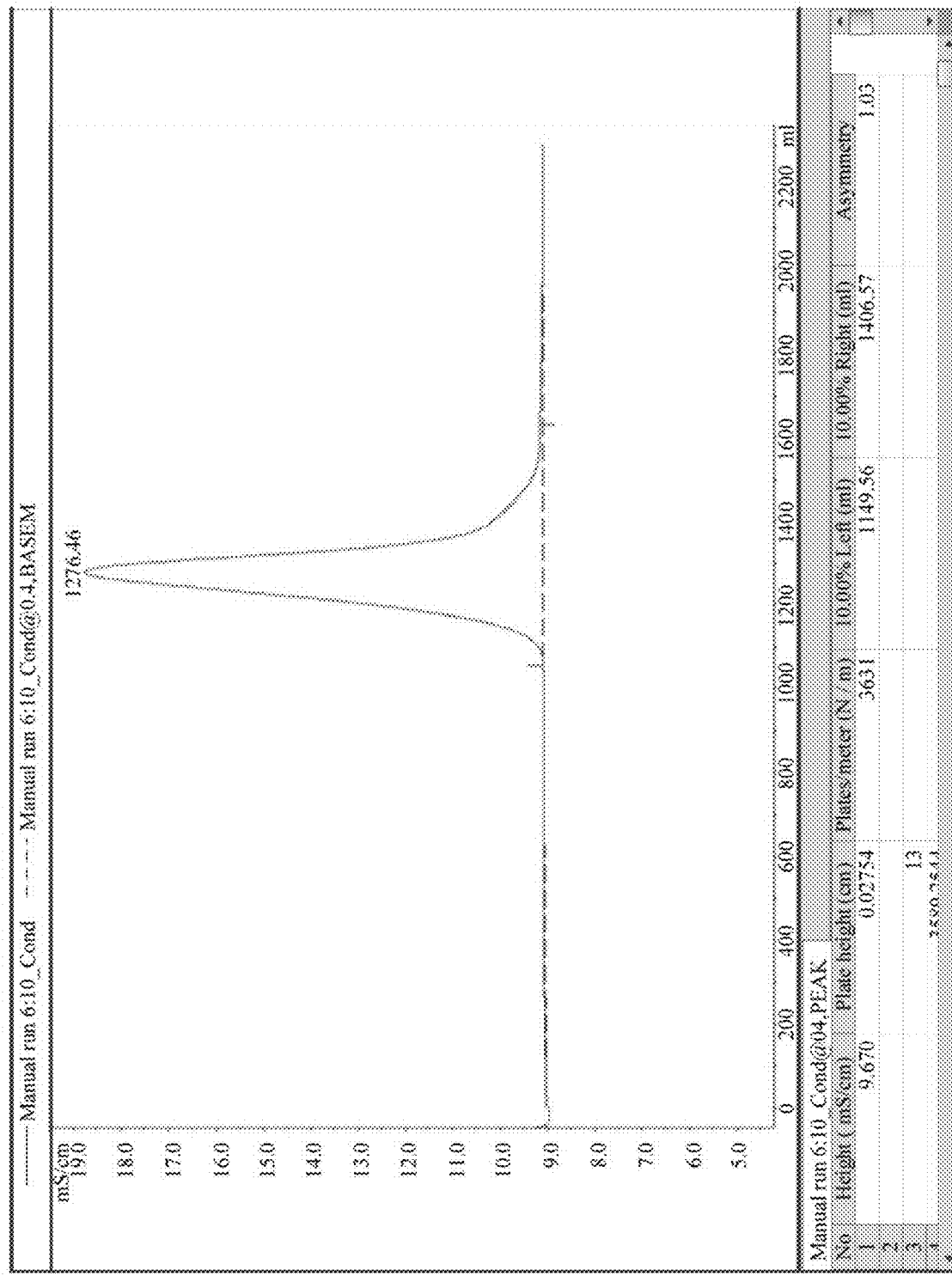

FIG. 10B shows the results of the Capto™ S Column #1 retest before gamma radiation.

Figure 10C:
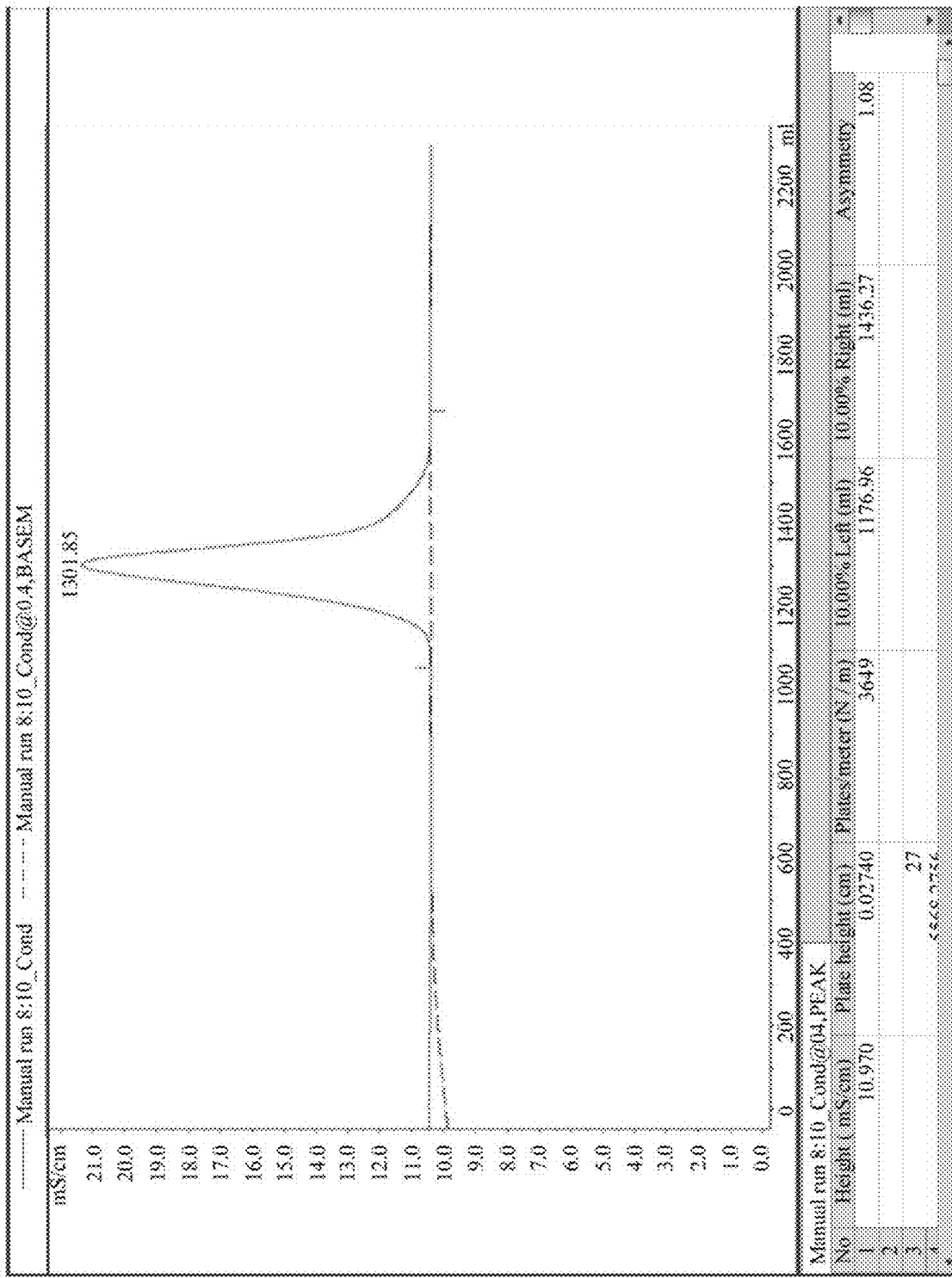

FIG. 10C shows the Capto™ S Column #1-10×20 cm—test before gamma radiation with the tubing set.

Figure 10D:
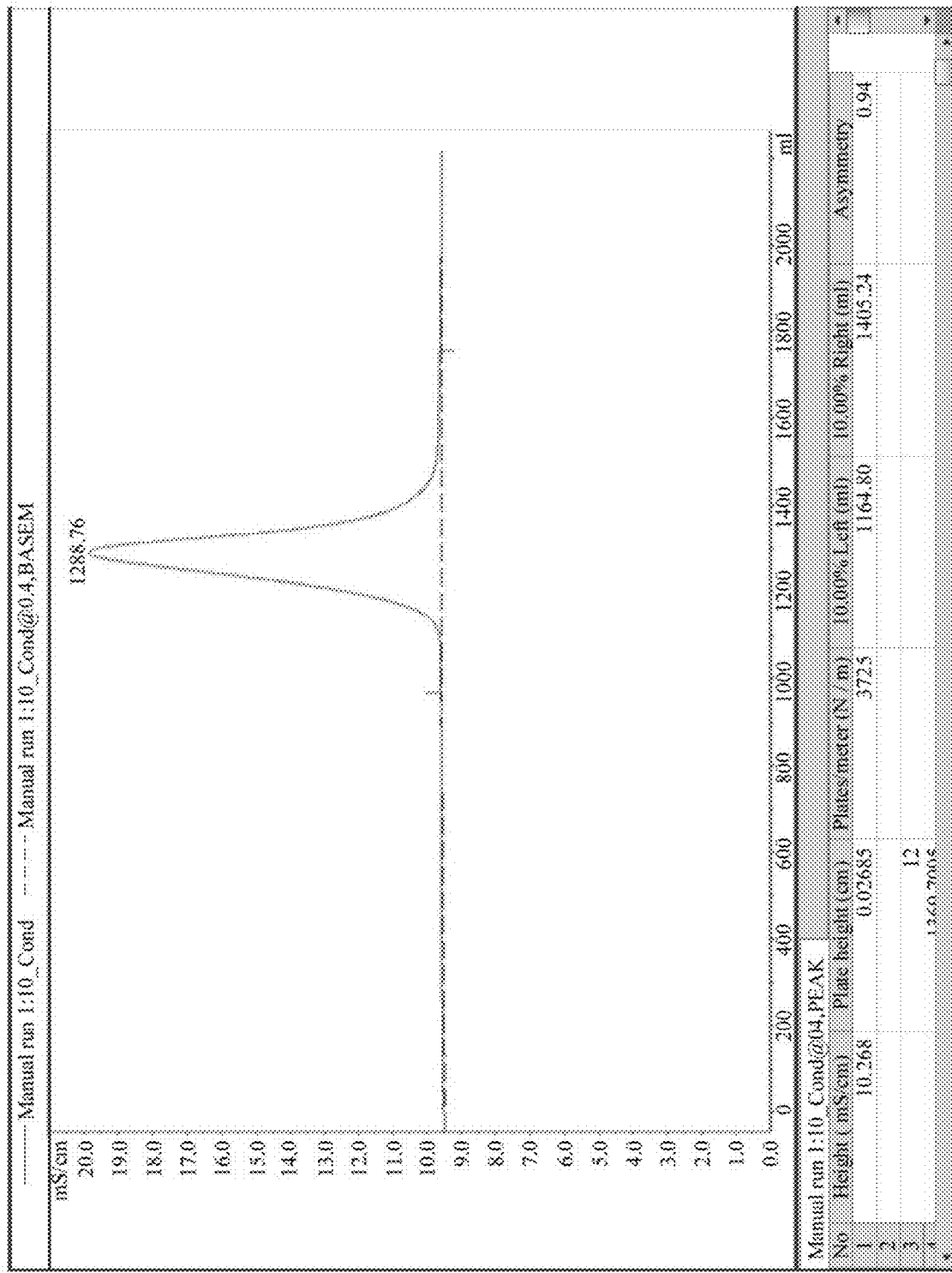

FIG. 10D shows the Capto™ S Column #2-10×20 cm—Initial test after packing.

Figure 10E:
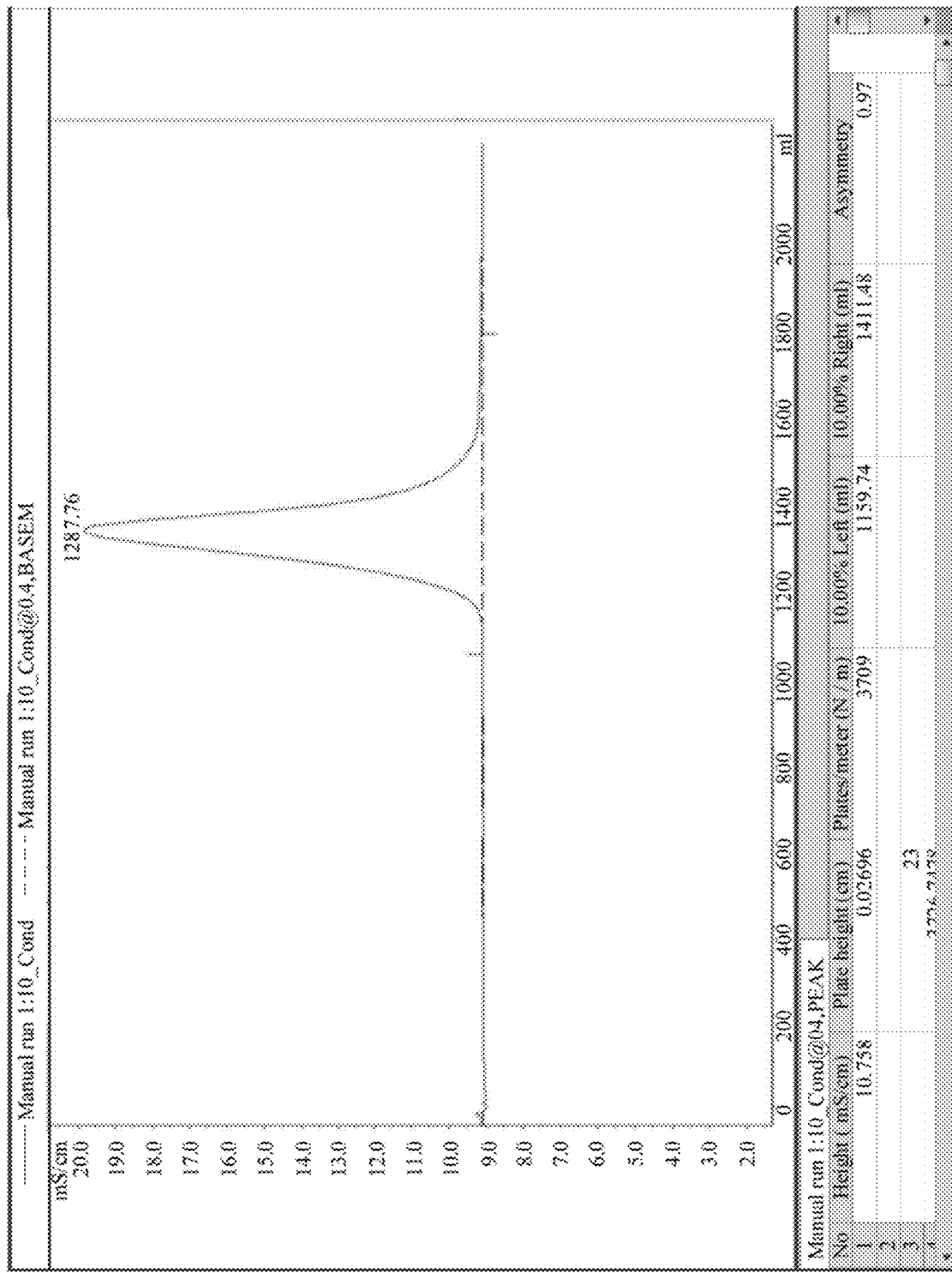

FIG. 10E shows the Capto™ S Column #2-10×20 cm—Retest before gamma radiation.

Figure 10F:
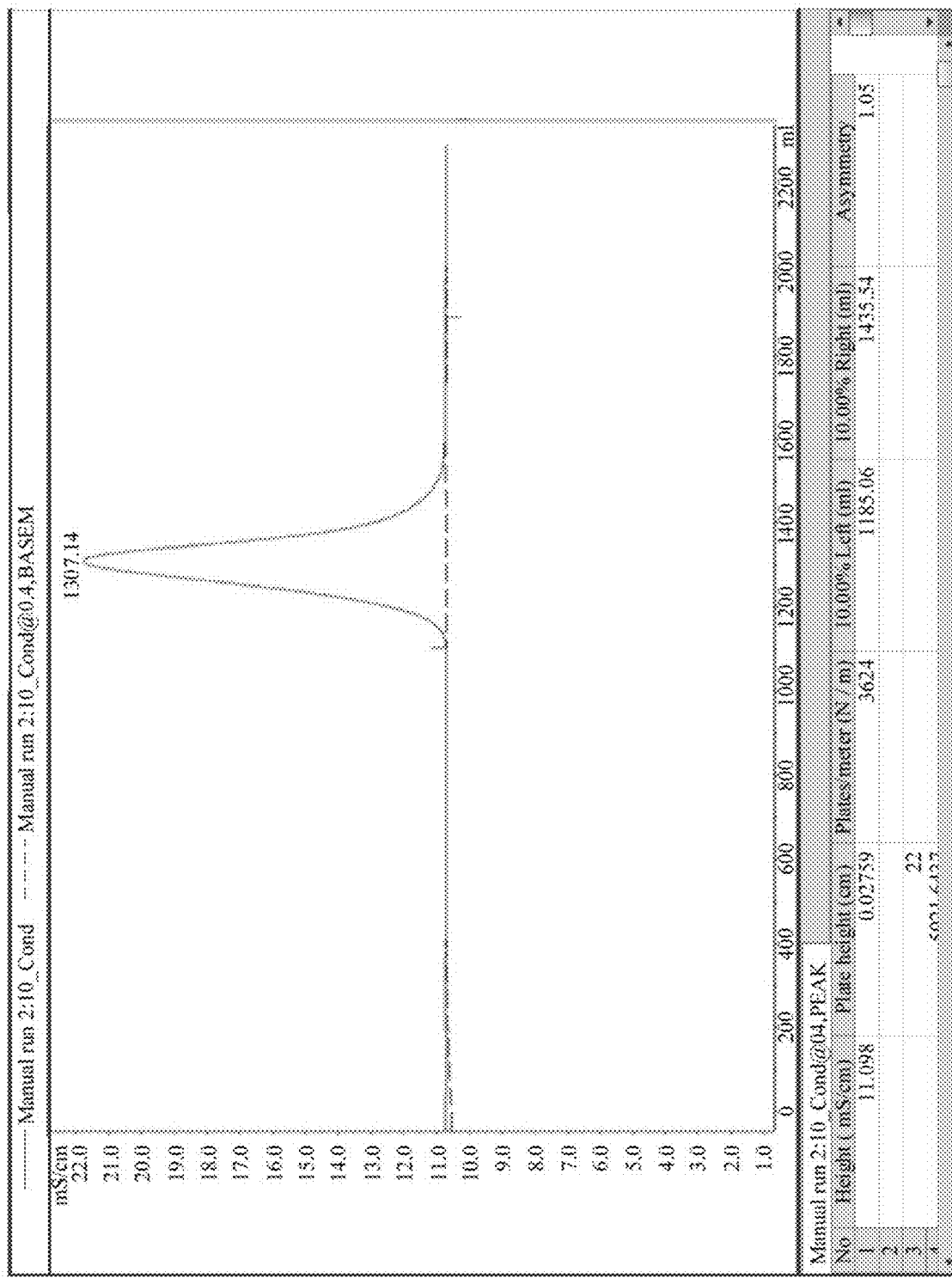

FIG. 10F shows the Capto™ S Column #2-10×20 cm—Test before gamma radiation with the tubing set.

Figure 10G:
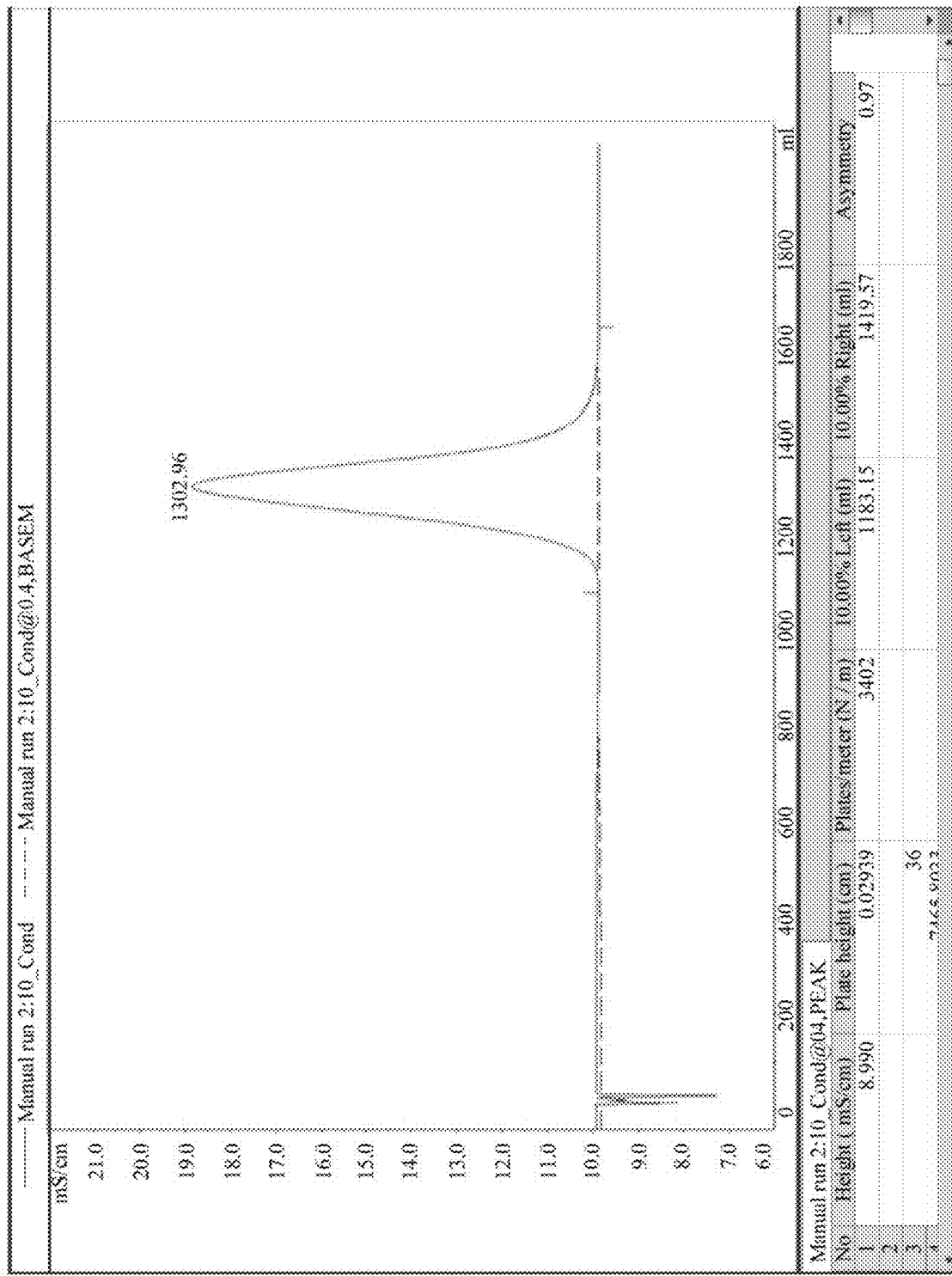
Figure 10H:
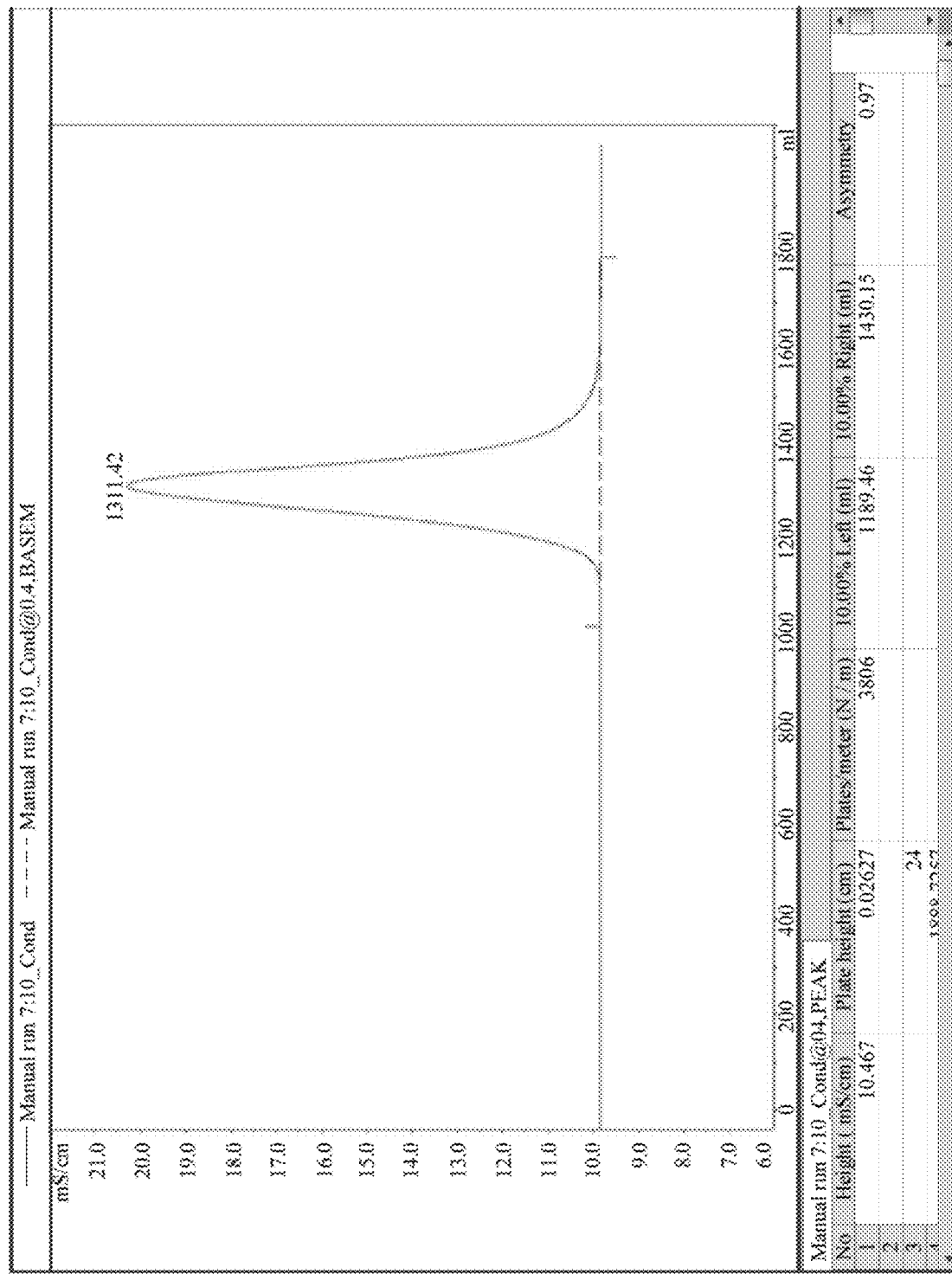

FIG. 10G shows the Capto™ S Column #2—post-gamma test—priming of the tubing set only (no upflow through the column).

FIG: 10H shows the Capto™ S Column #2—post-gamma test—after 1 CV column upflow.

Figure 10I:
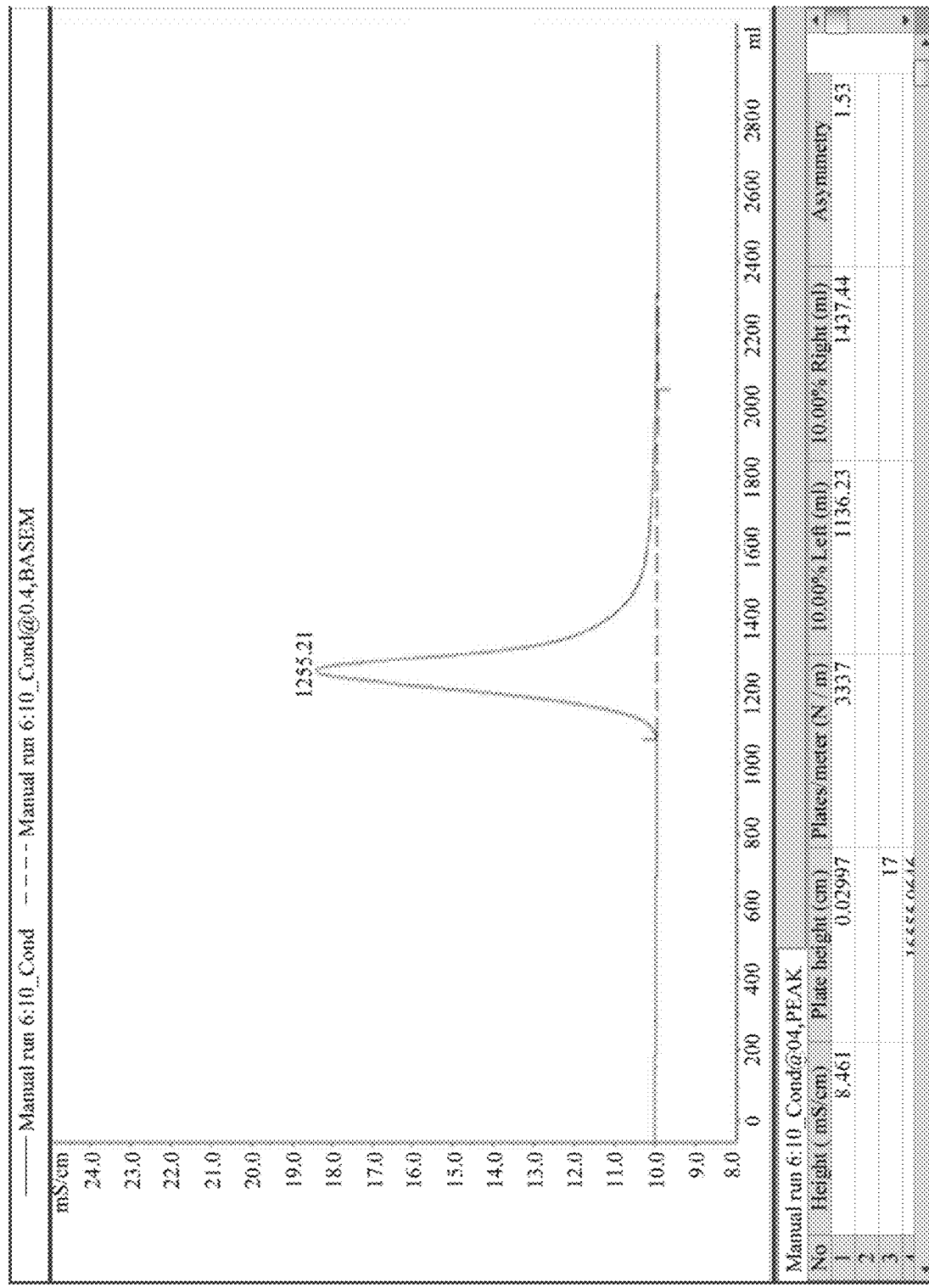

FIG. 10I shows the Capto™ S Column #1—post-gamma test—priming of the tubing set only (no upflow through the column).

Figure 10J:
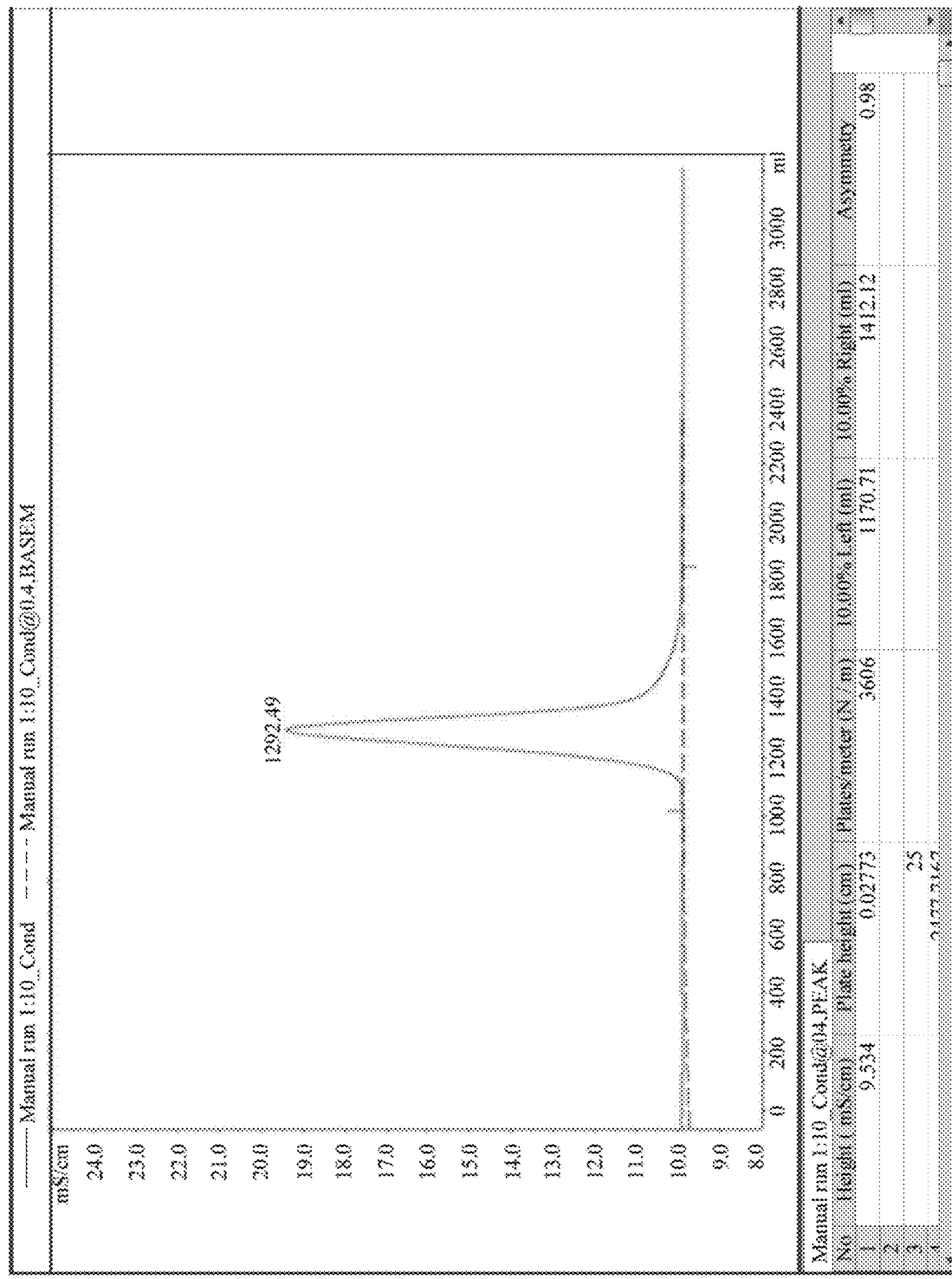

FIG. 10J shows Capto™ S Column #1 in a post-gamma test—after 1 CV upflow with tubing set Example 3

Post Gamma Irradiation Pressurization

During the process of gamma irradiation, gasses and pressurization occur within the closed column and tubing set assembly, which can negatively affect column usability. As describe in Example 2 the use of a tubing and valve set as described herein can remove these gasses and excess pressure from the column.

The goal of the present experiment was to demonstrate that gamma irradiation results in pressurization of the column, tubing and valve set, and/or column and tubing and valve set assembly. Two pre-packed OPUS® columns (Repligen Corporation) were used. Each pre-packed column had dimensions of 10 cm inner diameter and a 20 cm bed height packed with GE Healthcare Capto™ S, an agarose based cation exchange resin. For this experiment, both columns were attached a length of tubing to the inlet and outlet of the column with a pressure sensor attached to the inlet tubing.

Post-gamma irradiation, both column pressure sensors were read and pressurization of the column with tubing set were observed (Table 2).

In conclusion, gamma irradiation results in the pressurization of the column tubing set assembly. With the attachment of the tubing set 30 described thus far, successful removal of gas bubbles would also aides in the de-pressurization of the column, tubing set, or both.

TABLE 2

| Capto™ S | Pressure Measured Post Gamma Irradiation (PSIG) |
|---|---|
| Column # 3 10 × 20.5 cm | 7.98 |
| Column # 4 10 × 20.6 cm | 13.48 |

OTHER EMBODIMENTS

A number of embodiments of the invention have been described. Nevertheless, it will be understood that various modifications may be made without departing from the spirit and scope of the invention. Accordingly, other embodiments are within the scope of the following claims.

What is claimed is:

1. A method of removing entrapped gas, pressure, or both gas and pressure from a pre-packed chromatography column having a chamber, and a column tube having a column tube inlet and a column tube outlet, the method comprising:
   (a) obtaining a tubing and valve set comprising:
      tubing, a tubing inlet, a tubing outlet, a first valve disposed between the tubing inlet and the column tube inlet, and a second valve disposed between the column tube outlet and the tubing outlet, the tubing and valve set configured to define at least two different fluid paths each fluidly connected to the column tube inlet and the column tube outlet; and
      first and second tubing branches connected between the tubing inlet and the tubing outlet, a third valve disposed in the first tubing branch, and a fourth valve disposed in the second tubing branch,
   (b) either:
      (i) attaching the tubing inlet of the tubing and valve set to the column tube inlet and attaching the tubing outlet to the column tube outlet and then sterilizing the connected pre-packed chromatography column and the tubing and valve set, or
      (ii) sterilizing the pre-packed chromatography column and the tubing and valve set and then attaching the tubing inlet of the tubing and valve set to the column tube inlet and attaching the tubing outlet to the column tube outlet in a manner that maintains sterility of both the column and the tubing and valve set;
   (c) attaching the sterile tubing and valve set to a sterile or aseptic fluid source and to a fluid outlet;
      wherein when, a first flow path of the at least two different fluid paths enables fluid to flow from the tubing inlet, to the column tube outlet, to the column tube inlet, and to the tubing outlet; and wherein when the first and second valves are in an open configuration and the third and fourth valves are in a closed configuration, a second flow path of the at least two different fluid paths enables fluid to flow from the tubing inlet, to the column tube inlet, to the column tube outlet, and to the tubing outlet;

(d) configuring the first and second valves in a closed configuration and configuring the third and fourth valves in an open configuration; and (e) pumping sterile or aseptic liquid from the sterile or aseptic fluid source along the tubing and valve set into the column tube inlet and out from the column tube outlet along the first flow path, thereby removing any entrapped gas, pressure, or both gas and pressure from the chamber and the tubing along the first flow path without breaching the sterility of the pre-packed chromatography column and the tubing and valve set.

2. The method of claim 1, further comprising configuring the first and second valves in an open configuration and configuring the third and fourth valves in a closed configuration and pumping the sterile or aseptic liquid from the sterile or aseptic fluid source along the tubing and valve set into the column tube outlet and out from the column tube inlet along the second flow path.

3. The method of claim 1, said pumping comprises pumping said sterile or aseptic liquid in an amount equivalent to 0.1 or more volumes of the chamber.

4. The method of claim 1, comprising venting pressure from the tubing and valve set via a vent filter disposed in a third tubing branch coupled between the tubing inlet and the column inlet.

5. The method of claim 1, further comprising receiving expansion fluid into an expansion bag disposed in a third tubing branch coupled between the tubing inlet and the column inlet.

6. The method of claim 1, further comprising receiving expansion fluid into an expansion bag disposed in a third tubing branch coupled between the tubing inlet and the tubing outlet.

7. The method of claim 1, further comprising coupling the pre-packed chromatography column and tubing and valve set to a chromatography system.

8. The method of claim 1, further comprising disposing of the column tube after a single use of the column tube in a chromatography process.

9. The method of claim 1, wherein said step of sterilizing the pre-packed chromatography column and the tubing and valve set comprises sterilizing to a sterility assurance level (SAL) of $10^{-3}$ or better.

10. The method of claim 1, further comprising venting gas from the pre-packed chromatography column and the tubing and valve set via a vent filter disposed in a third tubing branch coupled between the tubing inlet and the column inlet.

11. The method of claim 1, wherein at least one of the at least two different fluid paths is configured to enable an upflow of the sterile or aseptic liquid through the chamber.

12. A method of removing entrapped gas and/or pressure from a pre-packed chromatography column having a chamber, and a column tube having a column tube inlet and a column tube outlet, the method comprising:

(a) obtaining a tubing and valve set comprising:
tubing, a tubing inlet, a tubing outlet, a first valve disposed between the tubing inlet and the column tube inlet, and a second valve disposed between the column tube outlet and the tubing outlet, the tubing and valve set configured to define at least two different fluid paths each fluidly connected to the column tube inlet and the column tube outlet; and
first and second tubing branches connected between the tubing inlet and the tubing outlet, a third valve disposed in the first tubing branch, and a fourth valve disposed in the second tubing branch, (b) (i) attaching the tubing inlet of the tubing and valve set to the column tube inlet and attaching the tubing outlet to the column tube outlet and then sterilizing the connected pre-packed chromatography column and the tubing and valve set, or (b) (ii) sterilizing the pre-packed chromatography column and the tubing and valve set and then attaching the tubing inlet of the tubing and valve set to the column tube inlet and attaching the tubing outlet to the column tube outlet in a manner that maintains sterility of both the column and the tubing and valve set;

(c) attaching the sterile tubing and valve set to a sterile or aseptic fluid source and to a fluid outlet;
wherein a first flow path of the at least two different fluid paths enables fluid to flow from the tubing inlet, to the column tube outlet, to the column tube inlet, and to the tubing outlet; and
wherein when the first and second valves are in an open configuration and the third and fourth valves are in a closed configuration, a second flow path of the at least two different fluid paths enables fluid to flow from the tubing inlet, to the column tube inlet, to the column tube outlet, and to the tubing outlet;

(d) closing the first and second valves and opening the third and fourth valves; and (e) pumping sterile or aseptic liquid from the sterile or aseptic fluid source along the first flow path to remove entrapped gas and/or pressure from the chamber and the tubing along the first flow path.

13. The method of claim 12, further comprising configuring the first and second valves in an open configuration and configuring the third and fourth valves in a closed configuration and pumping the sterile or aseptic liquid from the sterile or aseptic fluid source along the tubing and valve set into the column tube outlet and out from the column tube inlet along the second flow path.

14. The method of claim 12, comprising venting pressure from the tubing and valve set via a vent filter disposed in a third tubing branch coupled between the tubing inlet and the column inlet.

15. The method of claim 12, further comprising receiving expansion fluid into an expansion bag disposed in a third tubing branch coupled between the tubing inlet and the column inlet.

16. The method of claim 12, further comprising receiving expansion fluid into an expansion bag disposed in a third tubing branch coupled between the tubing inlet and the tubing outlet.

17. The method of claim 12, further comprising coupling the pre-packed chromatography column and tubing and valve set to a chromatography system.

18. The method of claim 12, further comprising disposing of the column tube after a single use of the column tube in a chromatography process.

19. The method of claim 12, further comprising venting gas from the pre-packed chromatography column and the tubing and valve set via a vent filter disposed in a third tubing branch coupled between the tubing inlet and the column inlet.

\* \* \* \* \*